(12) United States Patent
Hotokebuchi et al.

(10) Patent No.: US 7,955,394 B2
(45) Date of Patent: Jun. 7, 2011

(54) ARTIFICIAL KNEE JOINT

(75) Inventors: Takao Hotokebuchi, Saga (JP); Yasuju Takano, Osaka (JP)

(73) Assignees: Saga University, Saga (JP); Japan Medical Materials Corporation, Osaka (JP)

( * ) Notice: Subject to any disclaimer, the term of this patent is extended or adjusted under 35 U.S.C. 154(b) by 159 days.

(21) Appl. No.: 11/988,732

(22) PCT Filed: Jul. 13, 2006

(86) PCT No.: PCT/JP2006/313986
§ 371 (c)(1),
(2), (4) Date: May 22, 2008

(87) PCT Pub. No.: WO2007/007841
PCT Pub. Date: Jan. 18, 2007

(65) Prior Publication Data
US 2009/0043395 A1    Feb. 12, 2009

(30) Foreign Application Priority Data
Jul. 14, 2005   (JP) ................................ 2005-205888

(51) Int. Cl.
*A61F 2/38* (2006.01)
(52) U.S. Cl. .................................. 623/20.14; 623/20.26
(58) Field of Classification Search ............... 623/20.29, 623/20.28, 20.31, 20.33, 20.15, 20.14
See application file for complete search history.

(56) References Cited

U.S. PATENT DOCUMENTS

| | | | |
|---|---|---|---|
| 4,298,992 A * | 11/1981 | Burstein et al. | 623/20.27 |
| 4,634,444 A * | 1/1987 | Noiles | 623/20.27 |
| 4,808,185 A | 2/1989 | Penenberg et al. | |
| 5,282,869 A | 2/1994 | Miyajima et al. | |
| 5,800,552 A * | 9/1998 | Forte | 623/20.27 |
| 6,123,729 A | 9/2000 | Insall et al. | |

(Continued)

FOREIGN PATENT DOCUMENTS

JP     4-158860    6/1992
(Continued)

OTHER PUBLICATIONS

International Search Report issued Oct. 3, 2006 in the International (PCT) Application No. PCT/JP2006/313986.

(Continued)

*Primary Examiner* — Alvin J Stewart
(74) *Attorney, Agent, or Firm* — Wenderoth, Lind & Ponack, L.L.P.

(57) ABSTRACT

The artificial knee joint includes a femoral component, a tibial tray and an insert plate fixed onto the top surface of the tibial tray. The femoral component includes a femoral articular surface and a cam that is provided on the rear end of the femoral articular surface and protrudes from the femoral articular surface, the insert plate includes a tibial articular surface that makes contact with the femoral articular surface and a cam-receiving slide surface that makes contact with the cam. When the knee is extended, the joint takes a first sliding state in which the femoral articular surface slides against the tibial articular surface. When the knee is bent at an angle in a range from 90 to 160 degrees, the joint shifts from the first sliding state to a second sliding state in which the cam slides on the cam-receiving slide surface. When the knee is bent deeply with a bending angle of 180 degrees, the second sliding state is assumed in which a resection surface of the femoral component and the rear end of the insert plate are offset.

5 Claims, 20 Drawing Sheets

U.S. PATENT DOCUMENTS

| | | | |
|---|---|---|---|
| 6,203,576 B1 * | 3/2001 | Afriat et al. | 623/20.27 |
| 6,402,786 B1 | 6/2002 | Insall et al. | |
| 6,443,991 B1 * | 9/2002 | Running | 623/20.27 |
| 6,699,291 B1 * | 3/2004 | Augoyard et al. | 623/20.27 |
| 6,730,128 B2 * | 5/2004 | Burstein | 623/20.27 |
| 7,351,263 B2 * | 4/2008 | Afriat | 623/20.27 |
| 7,658,767 B2 * | 2/2010 | Wyss | 623/20.29 |
| 2005/0154472 A1 * | 7/2005 | Afriat | 623/20.29 |
| 2006/0265080 A1 * | 11/2006 | McMinn | 623/20.27 |
| 2009/0043395 A1 * | 2/2009 | Hotokebuchi et al. | 623/20.29 |
| 2009/0319048 A1 * | 12/2009 | Shah et al. | 623/20.29 |
| 2009/0326665 A1 * | 12/2009 | Wyss et al. | 623/20.21 |
| 2009/0326666 A1 * | 12/2009 | Wyss et al. | 623/20.29 |

FOREIGN PATENT DOCUMENTS

| | | |
|---|---|---|
| JP | 9-94261 | 4/1997 |
| JP | 10-155824 | 6/1998 |
| JP | 11-313845 | 11/1999 |
| JP | 3087344 | 8/2002 |
| JP | 102 01 744 | 2/2004 |
| JP | 2004-166802 | 6/2004 |

OTHER PUBLICATIONS

"Bi-Surface Total Knee System"; Kyocera; Version 5.0, 2002.

* cited by examiner (A)

(B)

Internal rotation

ARTIFICIAL KNEE JOINT

BACKGROUND OF THE INVENTION

1. Field of the Invention

The present invention relates to an artificial knee joint used to restore the normal function of a knee joint that has been heavily deformed due to such disease as gonarthrosis or chronic articular rheumatism.

2. Description of the Related Art

An artificial knee joint comprises a femoral component fixed onto the distal portion of the femur, and a tibial component fixed onto the proximal portion of the tibia. As an example of an artificial knee joint, such a constitution has been known as a convex sliding surface having a spherical shape or a spheroid formed on a sliding portion located at the middle on the rear end of the femoral component, and a concave surface having a spherical shape or spheroid formed on a sliding portion located at the middle on the rear end of the tibial component (for example, Japanese Unexamined Patent Publication (Kokai) No. 4-158860). The convex sliding surface and the concave sliding surface fit to each other when the knee bends or stretches, so as to make a motion of sliding rotation against each other on the rear, thereby allowing a wide range of motion. Moreover, the convex sliding surface and the concave sliding surface are enabled to fit to each other and make a motion of sliding rotation while supporting a load on the main articular surface even when bending the knee, by setting the height $T_1$ of the convex sliding surface and the depth $T_2$ of the concave sliding surface to satisfy a relationship of $T_1 \leq T_2$.

Another artificial knee joint is known which has such a constitution that comprises a tibial component and a femoral component, wherein the articular surface of the femoral component extends smoothly from the distal condyle to the epicondyle, so as to allow motion over a range of at least 160 degrees (for example, Japanese Unexamined Patent Publication (Kokai) No. 11-313845).

However, the artificial knee joint disclosed in Japanese Unexamined Patent Publication (Kokai) No. 4-158860 undergoes osseous impingement, that is contact between the remainder of the femur and the femoral component, when bending of the knee reaches 150 degrees or more (refer, particularly, to FIG. 4 of Japanese Unexamined Patent Publication (Kokai) No. 4-158860). When osseous impingement occurs, the knee cannot bend anymore. The seiza position (Japanese sitting posture on tatami) requires bending of the knee at an angle of about 160 degrees. Therefore, there have been cases in which patients having an artificial knee joint implanted who cannot sit in seiza style.

It is effective for preventing the osseous impingement from occurring to properly trim the residual bone during the ostectomy operation to resect the joint from the femur. However, such an operation of resecting the bone requires an advanced osteotomy technique, and there is a demand for an artificial knee joint that prevents the occurrence of osseous impingement more easily.

The artificial knee joint disclosed in Japanese Unexamined Patent Publication (Kokai) No. 11-313845 enables deep bending of the knee with bending angles of up to 160 degrees while compressing the occurrence of osseous impingement, by such a constitution as a spine of the tibial component and a cam of the femoral component making contact and sliding against each other. However, should osseous impingement occur when the knee bends as deep as 160 degrees, so-called soft tissue impingement is expected to occur, in which the soft tissue that surrounds the knee joint contacts the remainder of the femur 3 or the femoral component 2. It is desired to avoid the soft tissue impingement since it may damage the soft tissue. It is effective for preventing the soft tissue impingement from occurring, to design the artificial knee joint so as to be capable of bending at angles of a greater range (range of motion) than the range of bending angles which the knee actually experiences in real life movements.

Also according to Japanese Unexamined Patent Publication (Kokai) No. 11-313845, the spine of the tibial component is formed from ultra-high molecular weight polyethylene (UHMWPE), and the contact area between the spine and the cam is small during the sliding motion of the cam of the femoral component. As a result, the surface of the spine that contacts the cam is subjected to localized severe wear even in a relatively short period of use, thus making it inevitable to carry out an additional operation to replace the artificial knee joint.

SUMMARY OF THE INVENTION

Accordingly, in order to avoid both osseous impingement and soft tissue impingement while engaging in ordinary daily activities, it is desirable to use an artificial knee joint that allows bending of the knee at angles over an expanded range, at least 160 degrees. An object of the present invention is to provide an artificial knee joint having a range of motion of 160 degrees or more in bending angle.

Another object of the present invention is to provide an artificial knee joint that can reliably prevent osseous impingement from occurring regardless of how much the femur has been resectd for trimming.

Still another object of the present invention is to provide an artificial knee joint that can be used over an extended period of time by minimizing localized severe wear of component parts of the artificial knee joint.

In a conventional artificial knee joint, a sliding part (insert plate) of the tibial component is formed from ultra-high molecular weight polyethylene (UHMWPE). The insert plate wears, albeit slightly, since it slides in contact with the femoral component that is made of a metal or ceramics. It has been known that the insert plate becomes thinner through use over a long period of time after being implanted in a human body. Therefore, it is a common practice to design the insert plate with a predetermined thickness (normally from about 2 to 5 mm) taking the wear loss into account. However, since the slide surface of the insert plate is normally a concave surface that is recessed from the top surface of the insert plate, the overall thickness of the insert plate must be made larger than the above-mentioned predetermined thickness in order to ensure a sufficient thickness of the sliding surface. There has been such a problem that increasing the thickness of the insert plate leads to a greater amount of excision of the tibia, which increases the possibility of fracture after the operation.

Accordingly, a further object of the present invention is to provide an artificial knee joint that enables a decrease of the amount of excision while ensuring sufficient thickness of the slide surface of the insert plate.

A first artificial knee joint of the present invention comprises a femoral component fixed onto a distal portion of a femur, a tibial tray fixed onto a proximal portion of a tibia and an insert plate fixed onto a top surface of the tibial tray to receive the femoral component sliding thereon, the femoral component being provided with two curved femoral articular surfaces and a cam having a spheroidal or substantially cylindrical shape that is provided on the rear end of the femoral articular surface and protrudes from the femoral articular surface, the insert plate being provided with two tibial articular surfaces that make contact with the two femoral articular surfaces respectively and a cam-receiving slide surface that contacts the cam, wherein the artificial knee joint takes a first sliding state in which the femoral articular surface slides on the tibial articular surface when the knee is extended, a main contacting surface shifts from the first sliding state to a second sliding state in which the cam slides on the cam-receiving slide surface when the knee is bent at an angle between 90 to 160 degrees, and a resection surface of the femoral component and a rear end of the insert plate are offset in the second sliding state when the knee is bent deeply with a bending angle of 180 degrees.

In the present invention, the term "offset" means the departure between the resection surface of the femoral component and the rear end of the insert plate during deep knee bending with an angle of 180 degrees.

A second artificial knee joint of the present invention comprises a femoral component fixed onto a distal portion of a femur, a tibial tray fixed onto a proximal portion of a tibia and an insert plate fixed onto a top surface of the tibial tray to receive the femoral component sliding thereon, the femoral component being provided with two, medial and lateral, curved femoral articular surfaces, a connection that connects the rear ends of the two femoral articular surfaces, and an lateral femoral offset surface of a concave shape formed on the rear end of the lateral femoral articular surface, the insert plate being provided with two, medial and lateral, tibial articular surfaces that make slidable contact with the two femoral articular surfaces, a spine having, on the rear thereof, a curved surface that makes slidable contact with the connection, and an lateral tibial offset surface formed on the rear end of the insert plate so that the lateral femoral offset surface slides thereon, wherein the artificial knee joint takes a first sliding state in which the two medial and lateral femoral articular surfaces make slidable contact with the tibial articular surfaces when the knee is extended, the contact of the lateral articular surfaces in the first sliding state shifts to a third sliding state in which the lateral femoral offset surface makes slidable contact with the lateral tibial offset surface and to a fourth sliding state is formed in which the connection of the femoral component makes slidable contact with the rear curved surface of the spine of the insert plate when the knee is bent at an angle in a range from 90 to 160 degrees, and a resection surface of the femoral component and a rear end of the insert plate are offset in the third or fourth sliding state when the knee is bent deeply with a bending angle of 180 degrees.

According to the two artificial knee joints of the present invention, the resection surface of the femoral component and the rear end of the insert plate are separated, namely offset, from each other even when the knee is bent deeply at an angle of 180 degrees at which the resection surface of the femoral component and the rear end of the insert plate come closest to each other. This means that osseous impingement does not occur over a range of bending angles from 0 to 180 degrees, thus making it possible to deeply bend the knee with angles of up to 180 degrees in theory.

The first artificial knee joint and the second artificial knee joint have the common feature of achieving the offset state by shifting from the first sliding state, in which the femoral articular surface makes contact with the tibia articular surface, to the second sliding state to the fourth sliding state in which other parts make contact, but have different constitutions that are required to achieve the offset state.

In the first artificial knee joint, the offset state is achieved by shifting from the first sliding state to the second sliding state in which the cam slides in contact with the cam-receiving slide surface. In the first sliding state, osseous impingement occurs when the knee is bent at an angle from about 120 to about 160 degrees similarly to the case of the conventional artificial knee joint. According to the present invention, the femoral component and the insert plate are separated from each other so as to prevent osseous impingement from occurring even when the knee is bent deeply, by shifting from the first sliding state to the second sliding state before the osseous impingement occurs. Therefore, osseous impingement can be prevented from occurring without an advanced osteotomy technique, by personnel having only the basic operation technique for resecting the distal portion of the femur so as to match the resection surface configuration.

In the first artificial knee joint, stress is not localized since the contact area between the cam of the femoral component and the cam-receiving slide surface of the tibial component is larger than the contact area between the spine and the cam of the artificial knee joint disclosed in Japanese Unexamined Patent Publication (Kokai) No. 11-313845, even in the second sliding state. As a result, the artificial knee joint can be used over a long period of time while the insert plate is not likely to undergo localized severe wear.

In a healthy knee, internal rotation at an angle occurs in the knee from about 10 to about 30 degrees when sitting in seiza posture (sitting on the floor Japanese style). The artificial knee joint of the present invention also allows internal rotation to occur in the knee joint in the second sliding state, thus enabling natural motion of the knee joint.

In the second artificial knee joint, the offset state is achieved by the shifting of at least one of the two contact portions that are in contact in the first sliding state to the third sliding state in which the lateral femoral offset surface makes contact and slides with the lateral tibia offset surface. In the third sliding state, the lateral femoral offset surface formed on the rear end of the femoral component becomes hitched on the lateral tibia offset surface that is formed on the rear end of the insert plate, so that the lateral side of the femoral component moves slightly upward and backward. As a result, the femoral component and the insert plate move further apart from each other, and thereby osseous impingement can be prevented from occurring even during deep knee bending. Therefore, osseous impingement can be prevented from occurring without an advanced osteotomy technique, by personnel having the basic operation technique for resecting the distal portion of the femur so as to match the resection surface.

In the second artificial knee joint, since the lateral side of the femoral component moves backward when the third sliding state is formed, internal rotation of the femoral component automatically occurs so that natural motion of the knee joint can be achieved. The bending angle at which the internal rotation occurs and the extent of the internal rotation can be adjusted at will by adjusting the position where the lateral femoral offset surface is formed and/or the size of the lateral femoral offset surface.

In the second artificial knee joint, it is preferable that the fourth sliding state is formed in such a way as the connection that connects the rear portions of the two femoral articular surfaces makes contact with the rear curved surface of the spine, so that the femoral component does not shift forward when the third sliding state is formed.

The fourth sliding state corresponds to the sliding between the spine and the cam (which corresponds to the connection of the present invention) of the artificial knee joint disclosed in Japanese Unexamined Patent Publication (Kokai) No. 11-313845, where severe wear of the spine may cause a problem. According to the present invention, however, the femoral component is fully compressed from being displaced forward in the third sliding state, and therefore the only function of the fourth sliding state is to provide auxiliary compression of the forward displacement of the femoral component. As a result, load on the rear curved surface of the spine in the fourth sliding state is reduced to a lower level than in the case of Japanese Unexamined Patent Publication (Kokai) No. 11-313845, and therefore the spine is less likely to be severely worn.

In the first and second artificial knee joints of the present invention, shift must occur from the first sliding state to the second through fourth sliding states at a bending angle smaller than the bending angle at which osseous impingement occurs in the first sliding state. The bending angle at which the sliding state shifts can be adjusted by means of the size and shape of the cam and the cam-receiving slide surface in the first artificial knee joint, and by means of the position where the lateral femoral offset surface is formed and the size of the lateral femoral offset surface in the second artificial knee joint. The bending angle at which this shift takes place is called the offset angle in this specification. The offset angle can be set at will within a range from 90 to 160 degrees. Accordingly with a bending angle of 90 degrees or less at which the knee joint receives a significant load, the two articular surfaces make contact with each other so as to stabilize the knee while, with a bending angle of 160 degrees or more at which osseous impingement is inevitable in the first sliding state, the knee joint shifts to the second through fourth sliding state so as to avoid the occurrence of osseous impingement.

The artificial knee joint of the present invention has a movable range of bending angles from 0 to 180 degrees, and enables deep knee bending of up to 180 degrees in theory. This makes it possible, not only to make deep knee bending while avoiding Osseous impingement, but also to compress the occurrence of soft tissue impingement during deep knee bending. Therefore, the artificial knee joint of the present invention enables a patient whose knee joint has been replaced to walk with a stable knee condition, sit in seiza posture without pain, and live in comfort.

DETAILED DESCRIPTION OF THE INVENTION

First Embodiment

Figure 1:
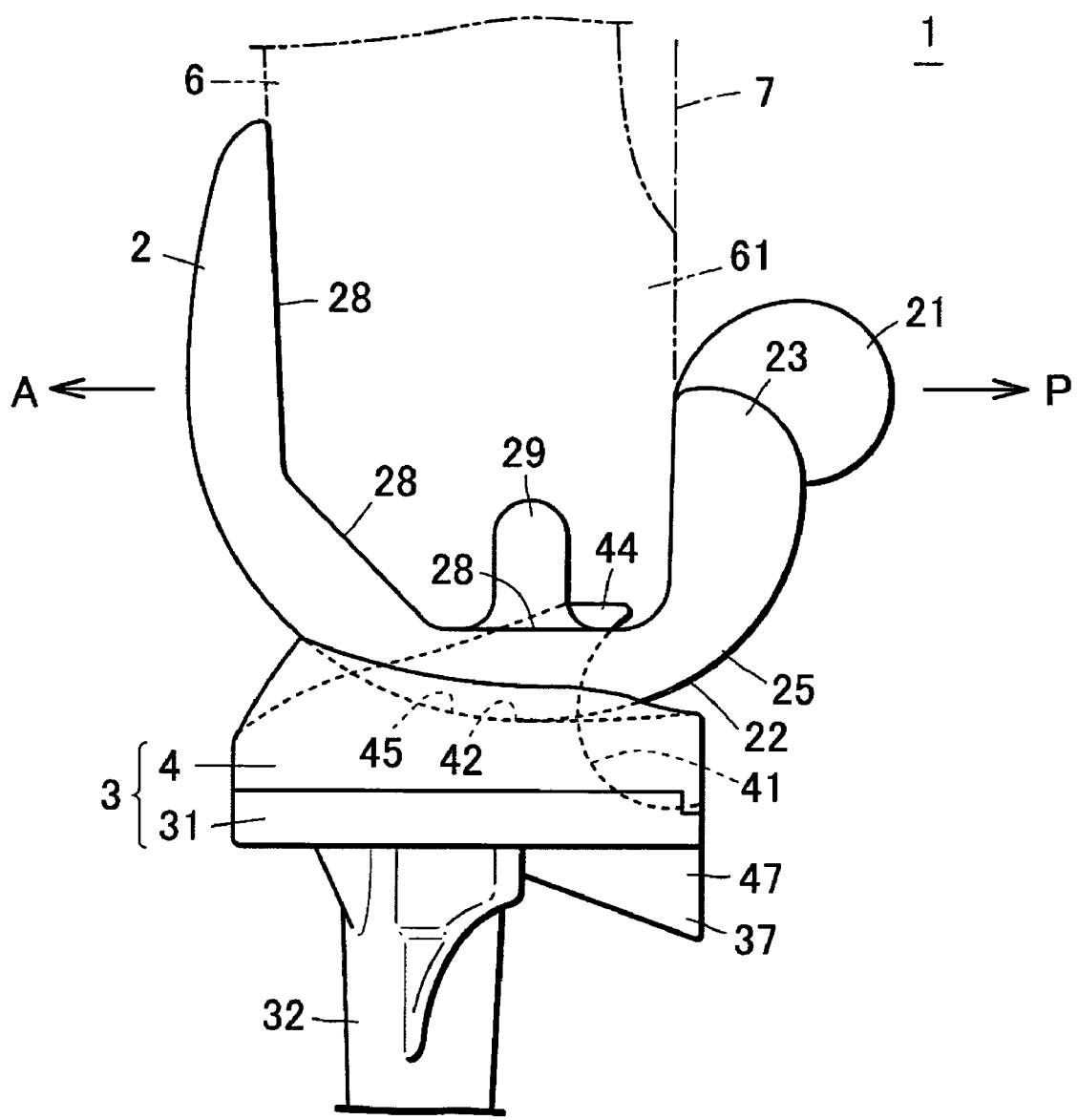
FIG. 1 is a side view of an artificial knee joint according to the first embodiment of the present invention.
Figure 2:
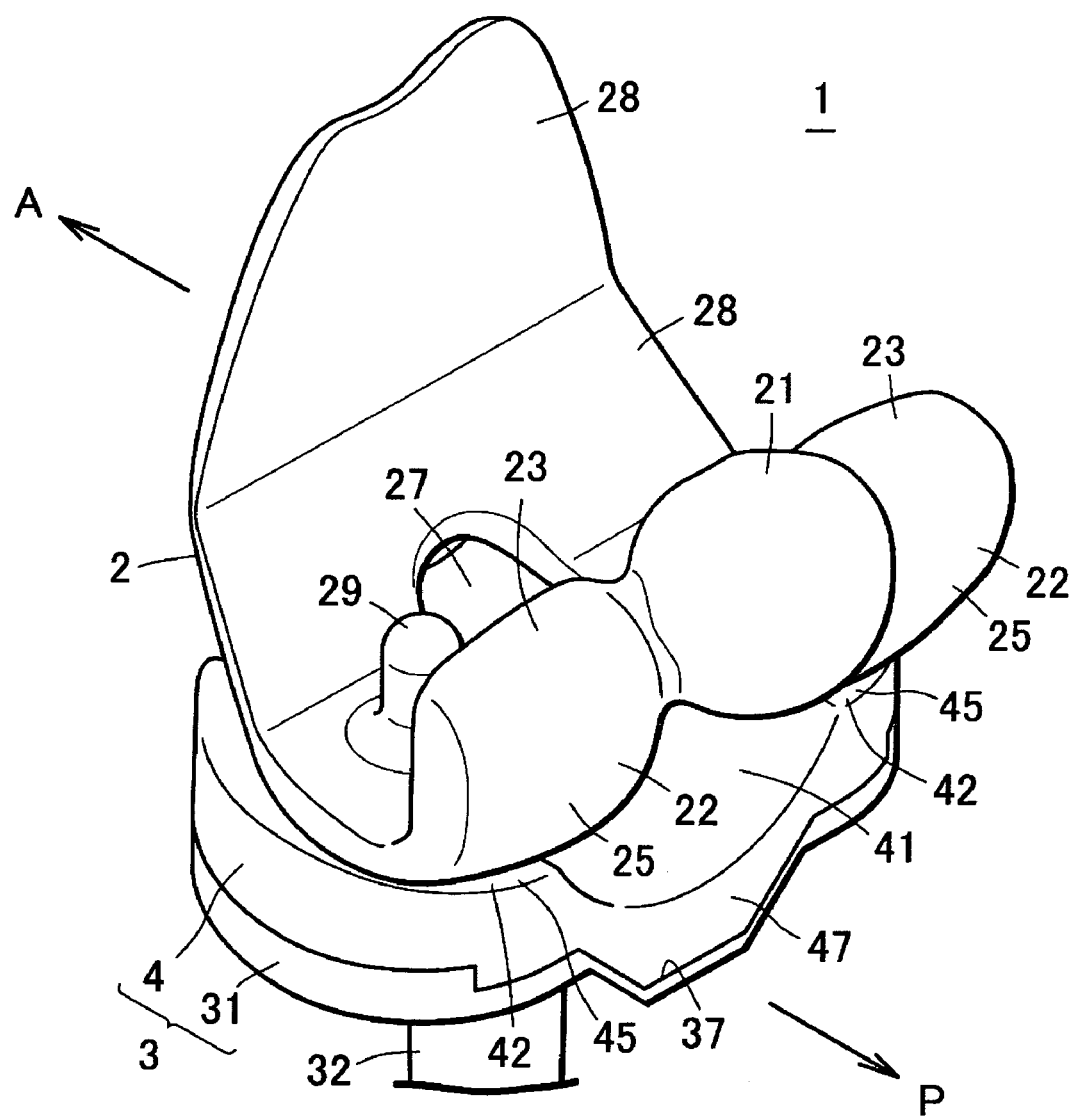
FIG. 2 is a perspective view of the artificial knee joint according to the first embodiment of the present invention.
Figure 3:
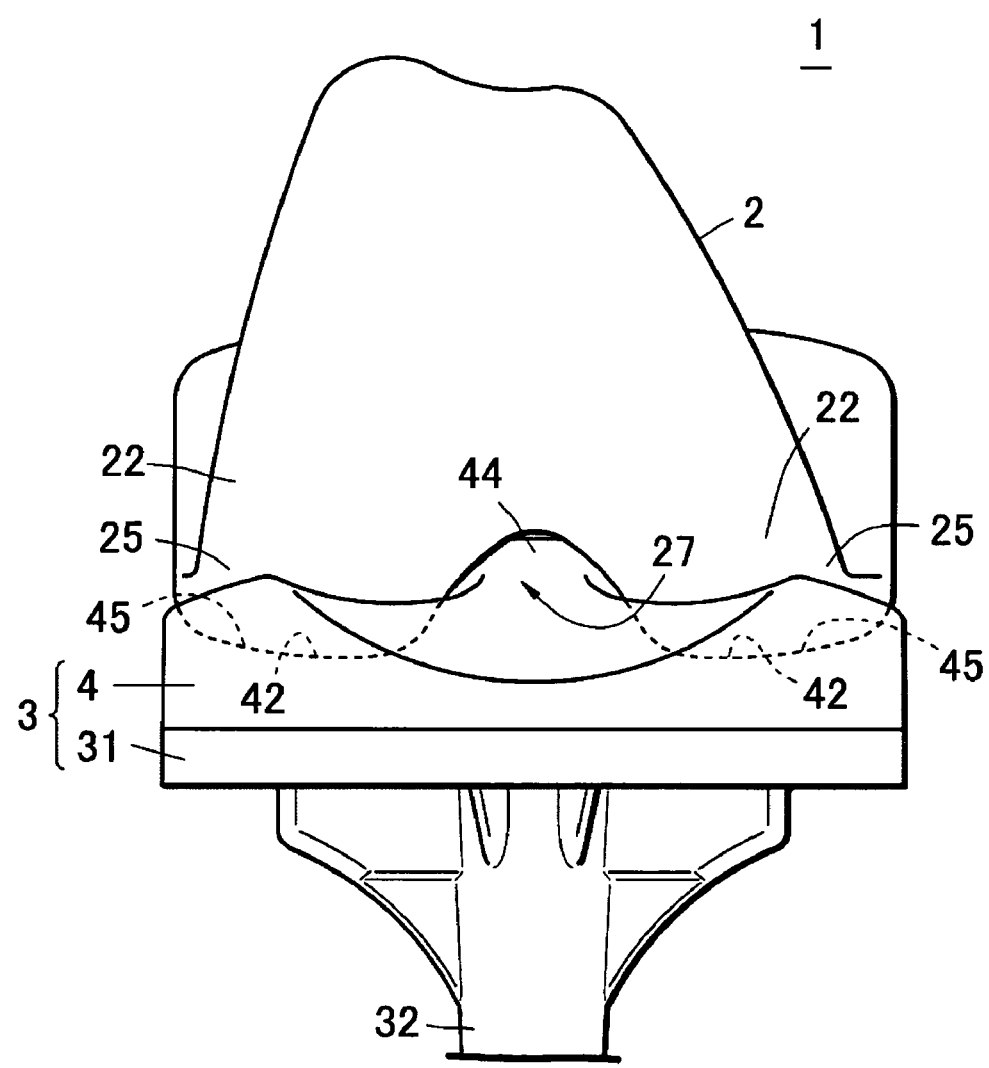
FIG. 3 is a front view of the artificial knee joint according to the first embodiment of the present invention.
Figure 4:
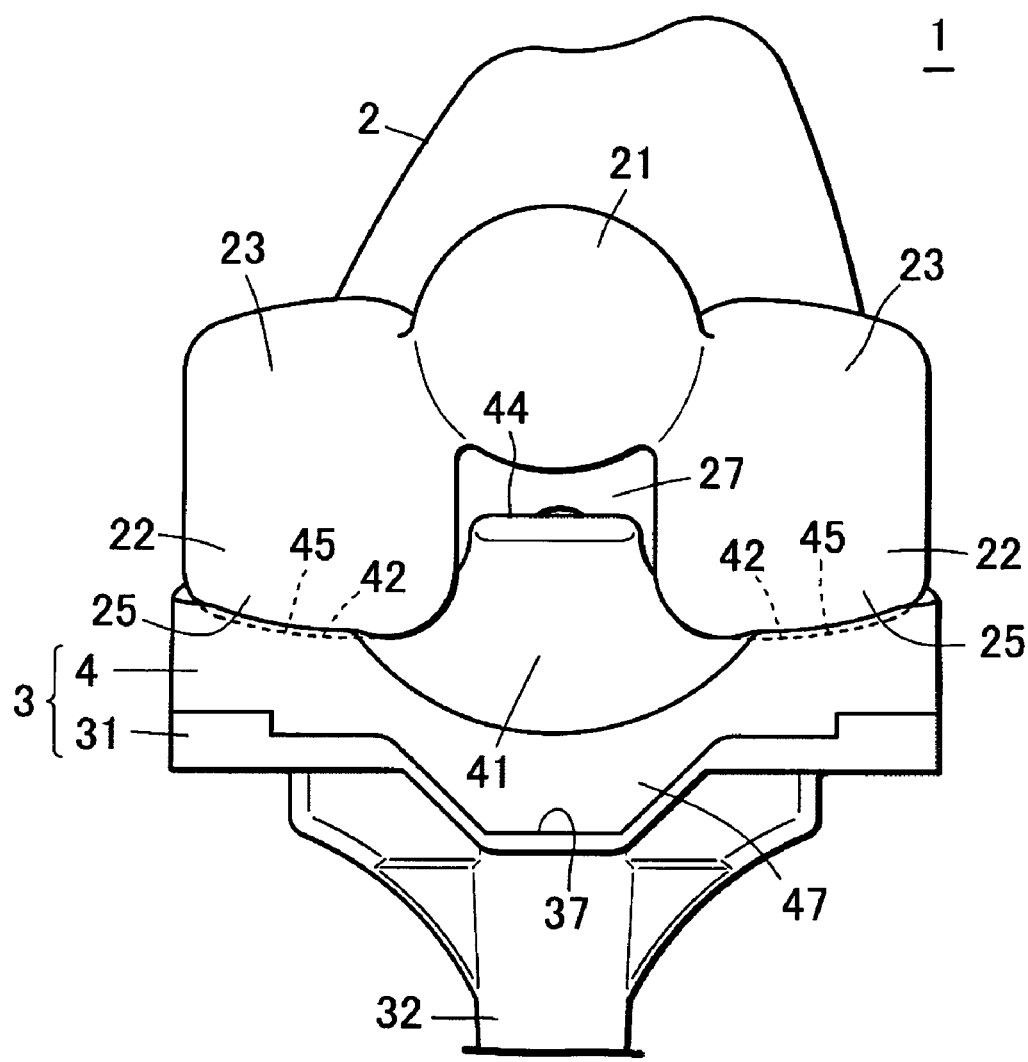
FIG. 4 is a rearview of the artificial knee joint according to the first embodiment of the present invention.
Figure 5:
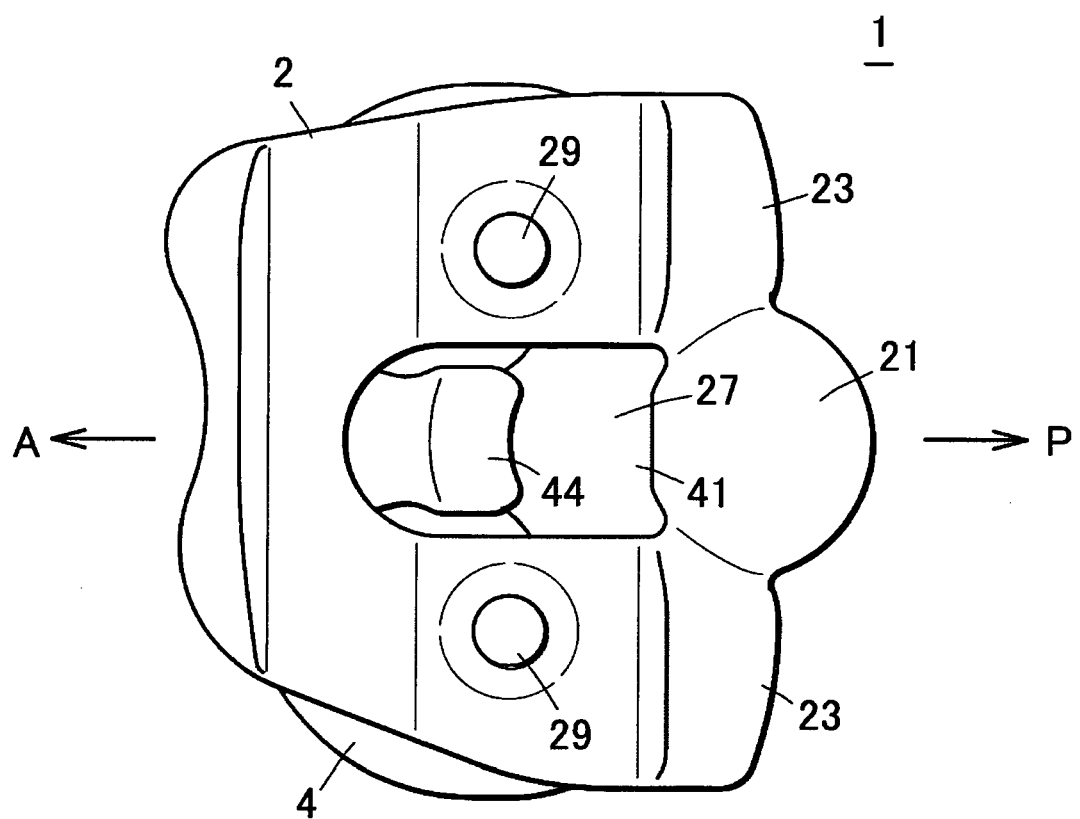
FIG. 5 is a top view of the artificial knee joint according to the first embodiment of the present invention.

An artificial knee joint 1 of the present invention comprises a femoral component 2 fixed onto the distal portion of the femur and a tibial component 3 fixed onto the proximal portion of the tibia as shown in FIGS. 1 through 5.

The femoral component 2 comprises two femoral articular surfaces 25 of bulging and curved shapes, and a cam 21 of spheroidal or substantially cylindrical shape that is provided on the rear end 23 of the femoral articular surface 25 and protrudes from the femoral articular surface 25.

The tibial component 3 comprises a tibial tray 31 fixed onto the proximal portion of the tibia and an insert plate 4 fixed onto the top surface of the tibial tray 31.

The insert plate comprises two tibia articular surfaces 45 that make contact respectively with the two femoral articular surfaces 25 and a cam-receiving slide surface 41 that contacts the cam 21 and slides against the femoral component 2 in contact therewith.

When the knee is extended, the artificial knee joint 1 of the first embodiment takes the first sliding state in which the femoral articular surface 25 slides against the tibial articular surface 45 in contact therewith. When the knee is bent at an angle in a range from 90 to 160 degrees, the joint begins to shift from the first sliding state to the second sliding state in which the main slide contact changes from between the femoral articular surface 25 and the tibial articular surface 45 to that between the cam 21 and the cam-receiving slide surface 41. When the knee is bent deeply to an angle of 180 degrees, the second sliding state is fully engaged so that the resection surface 7 of the femoral component 3 and the rear end of the insert plate 4 are offset.

FIG. 1 is a side view of the artificial knee joint 1 according to the first embodiment at a bending angle of 0 degrees, where the femur 6 extends vertically upward. The artificial knee joint 1 is used with the portion of the femoral component 2 extending upward while being disposed at a position shifted forward (direction indicated by arrow A) and the rear end 23 being disposed at a position shifted backward (direction indicated by arrow P).

The femoral component 2 has a deeply curved U-letter shape when viewed sideways, and is mounted so as to sandwich the end of the femur 6 on the front and back thereof, after the distal portion of femur 6 has been resected. Formed on the lateral surface of the femoral component 2 are two condyles 22 (protruding portions) that extend in the front-back direction, the surface being referred to as the femoral articular surface 25. The femoral articular surface 25 is finished to be very smooth so as to allow smooth sliding when the knee joint is bent.

The rear end 23 of the femoral component 2 has the cam 21 of spheroidal shape formed between the two condyles 22. The cam 21 protrudes significantly in the backward direction P from the femoral articular surface 25.

The medial side of the femoral component 2 serves as a femoral securing surface 28 that makes contact with the femur 6. An ailing femur is subjected to an ostectomy operation to remove the lesion of the joint bone, and to trim (resect) the joint bone so as to match the size and shape of the femoral securing surface 28 of the femoral component 2. A rear portion on the P side of the femur 6 is resected so as to match the shape of a plane called the resection surface 7 of femoral component 2, with a protruding portion called the residual bone 61 left to remain at the intersection of the profile curve of the femur 6 and the resection surface 7. Osseous impingement is often induced by the contact between the residual bone 61 and the tibial component 3, and may be mitigated by a technique that trims the femur 6 to reduce the protrusion of the residual bone 61. However, such a trimming operation requires an advanced osteotomy technique and may leave the residual bone 61 having such a shape as shown in the drawing, in many cases.

A ball 29 may be provided as required on the femoral securing surface 28 of the femoral component 2. The ball 29 is inserted into the femur so as to stabilize the state of the femoral component mounted therein. The femoral component 2 is fixed onto the femur as required by means of a bone cement. The femoral component 2 is formed from metal having high biocompatibility such as titanium alloy or cobalt-chromium alloy, or ceramics such as alumina or zirconia.

The insert plate 4 of the tibial component 3 is a member used to allow the femoral component 2 to slide thereon. The insert plate 4 has two sockets 42 (sockets refer to recessed parts) extending in the front-back direction, to allow the two condyles 22 of the femoral component 2 to slide therein. Each of the sockets 42 has the very smooth tibial articular surface 45 formed on the surface thereof, so that the femoral articular surface 25 of the femoral component 2 can slide smoothly thereon.

The insert plate 4 has a spine 44 formed near the center thereof, that protrudes from a slot 27 that is formed at the center of the femoral component 2 and extends in the front-back direction. The surface of the spine 44 on the back side P continues to the cam-receiving slide surface 41.

The cam-receiving slide surface 41 is formed in such a shape that accommodates the cam 21 of the femoral component 2. The cam-receiving slide surface 41 and the cam 21 are designed so as to make contact with each other when the artificial knee joint 1 bends beyond a predetermined angle, for example 90 degrees. Surfaces of the cam-receiving slide surface 41 and the cam 21 are both finished smooth so as to allow smooth sliding motion. The insert plate 44 is formed from ultra-high molecular weight polyethylene (UHMWPE).

The tibial tray 31 of the tibial component 3 is fixed, on the bottom surface thereof, onto the proximal portion of the tibia, and receives the insert plate 4 on the top surface. The tibial tray 31 has the function of distributing the load exerted by the femoral component 2 on the insert plate 4 so as to prevent stress from concentrating at a portion of the tibia. To fix the tibial tray 31, the lesion of the joint in the proximal portion of the tibia is resected first, followed by the insertion of the stem 32 of the tibial tray 31 into the tibia. After positioning the tibial tray so that the top surface thereof becomes substantially horizontal, the tibial tray 31 is fixed onto the tibia by means of a screw or bone cement.

The tibial tray 31 is formed from metal having high biocompatibility such as titanium alloy or cobalt-chromium alloy, or ceramics such as alumina or zirconia.

In the artificial knee joint 1 of the present invention, the sliding state that constitutes the main slide contact shifts from the first sliding state to the second sliding state through transition angles in a range from 90 to 160 degrees. The transition angle at which the sliding state shifts is the offset angle. The first sliding state takes place over a large contact area and is therefore suited to a situation where a large load is applied to the knee such as standing upright or walking. The second sliding state, in contrast, is not capable of bearing a heavy load on the knee although allows deep knee bending. Therefore, the offset angle is determined by balancing the load on the knee and the extent to which osseous impingement is to be avoided.

An offset angle less than 90 degrees causes a shift to the second sliding state when the knee is still under a large load which adversely affects the stability of the knee, and is therefore not desirable. An offset angle larger than 160 degrees allows the occurrence of osseous impingement in the first sliding state, and is therefore not desirable.

Figure 6:
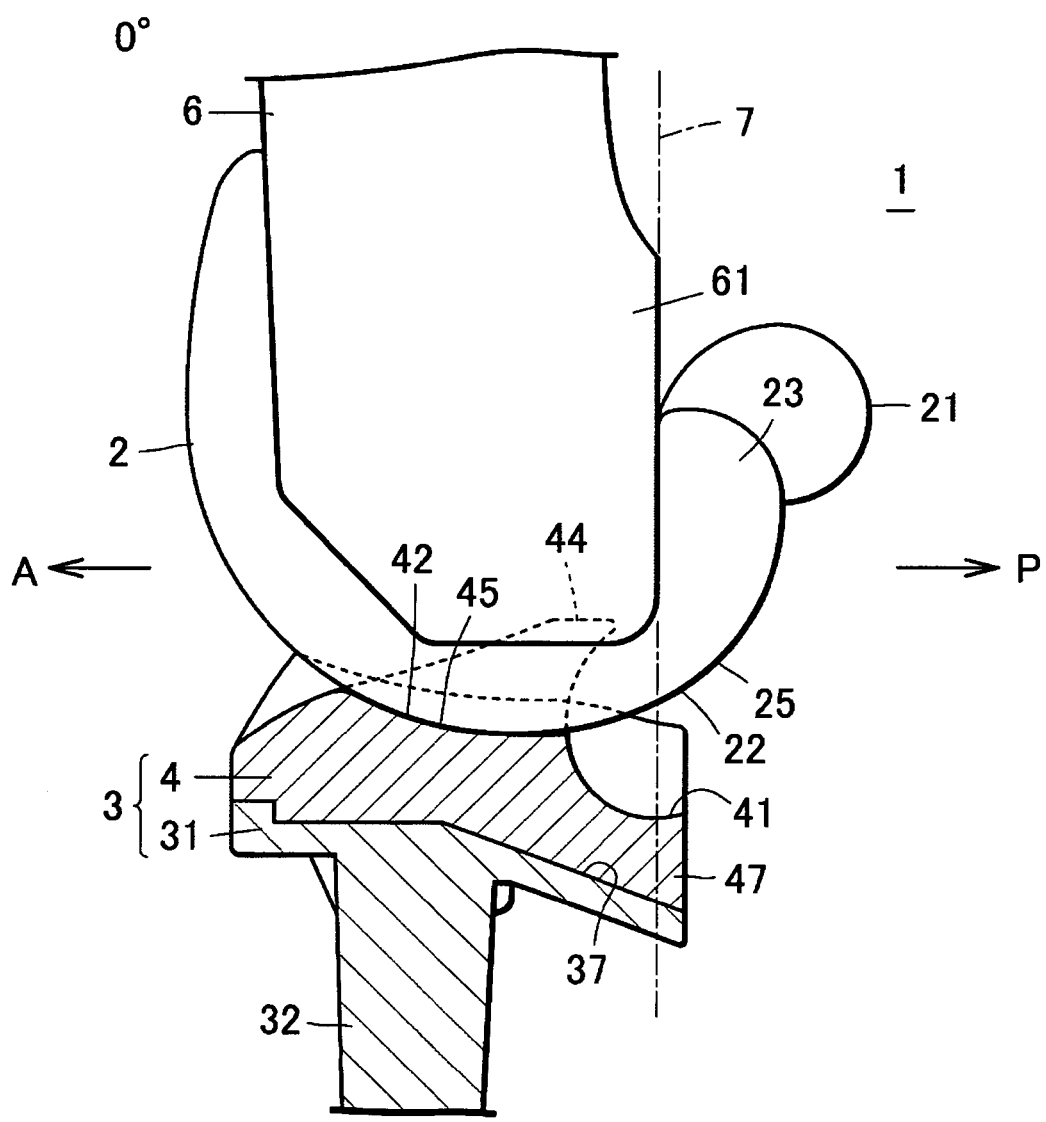
FIG. 6 is a side view of the artificial knee joint according to the first embodiment of the present invention, showing a bending motion with a bending angle of 0 degrees (the knee is extended).
Figure 7:
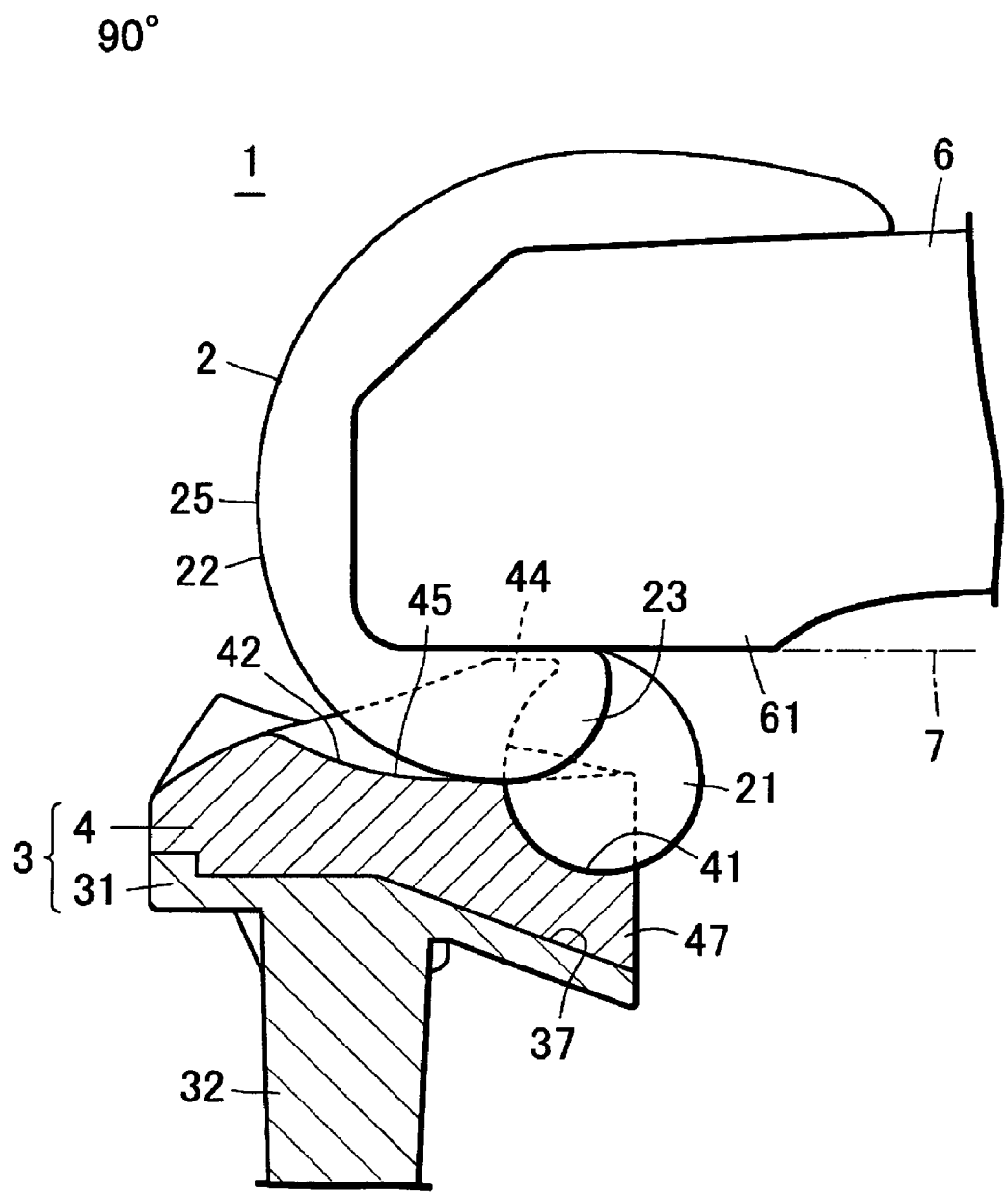
FIG. 7 is a side view of the artificial knee joint according to the first embodiment of the present invention, showing a bending motion with a bending angle of 90 degrees.
Figure 8:
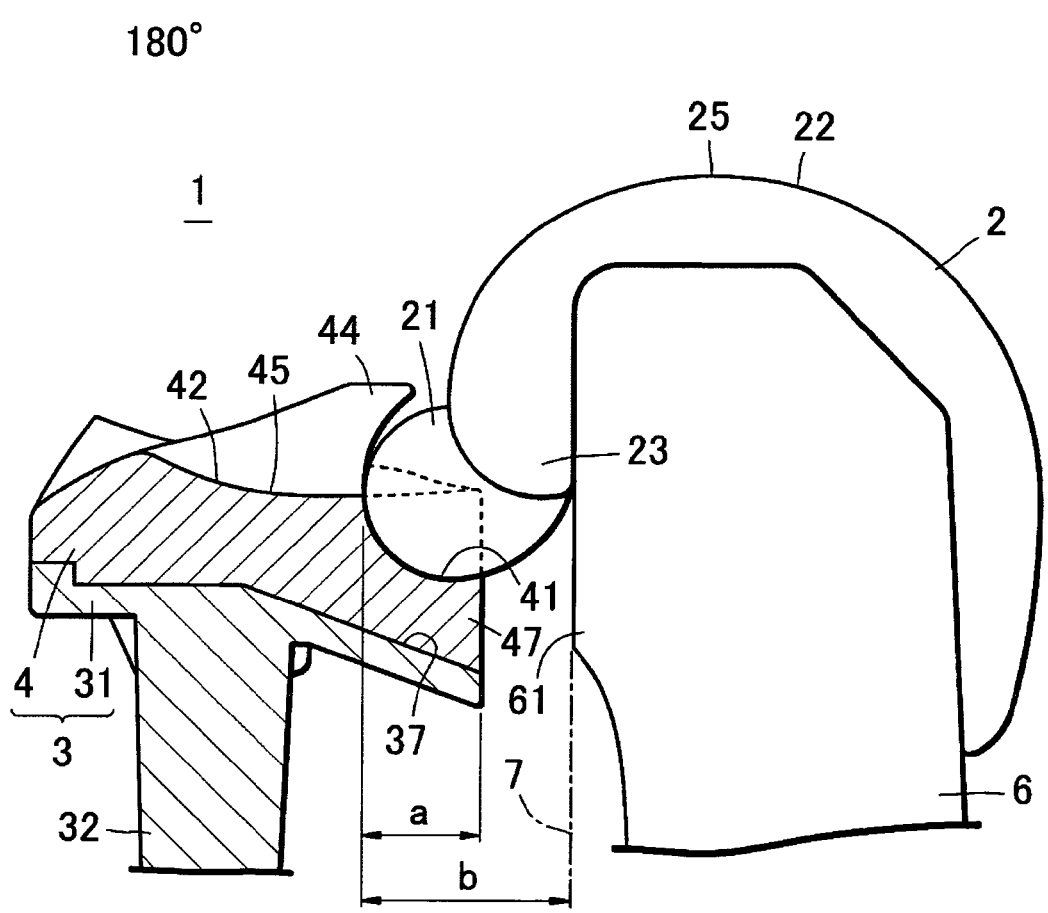
FIG. 8 is a side view of the artificial knee joint according to the first embodiment of the present invention, showing a bending motion with a bending angle of 180 degrees (deep knee bending).

The artificial knee joint of the present invention allows the knee to bend at angles from 0 to 180 degrees as shown in FIGS. 6 through 8. The offset angle of the artificial knee joint 1 is 90 degrees.

When the bending angle is 0 degrees (the knee is extended), the femoral articular surface 25 and the tibial articular surface 45 are in contact with each other thereby forming the first sliding state, as shown in FIG. 6. This state takes place when the person is standing upright or walking, causing a heavy load on the knee joint. The artificial knee joint of the present invention takes the first sliding state when the bending angle is 0 degrees, and is therefore capable of bearing the heavy load applied to the knee joint.

When the bending angle reaches the offset angle of 90 degrees, the joint shifts from the first sliding state to the second sliding state where the cam-receiving slide surface 41 and the cam 21 make contact with each other as shown in FIG. 7. The bending angle of 90 degrees is the maximum of bending angles that can take place when walking or climbing up or down a stairway, in which case the load applied to the knee joint is far less than that experienced with a bending angle of 0 degrees. Accordingly, loads applied to the knee joint with a bending angle of 90 degrees or more during routine activities in normal life can be born in the second sliding state. However, this does not apply to a case where heavy physical work is carried out with the knee bent deep, in which case the offset angle must be set larger.

As the bending angle of the knee joint is increased beyond the offset angle of 90 degrees of the artificial knee joint, the second sliding state formed by the cam-receiving slide surface 41 and the cam 21 becomes predominant. When the cam-receiving slide surface 41 and the cam 21 slide in contact with each other, the femoral component and the tibial component gradually depart from each other. Accordingly, the femoral articular surface 25 and the tibial articular surface 45 depart from each other while sliding, thereby canceling the first sliding state. In this way, the main contact surface shifts from the first sliding state to the second sliding state when the bending angle is larger than the offset angle. For the most part of the second sliding state, the knee joint receives less load in such situations as sitting on a chair or sitting in seiza posture. As a result, the problem of the knee joint becoming unstable hardly occurs even in the second sliding state where the load bearing capability is low. In this embodiment, the offset angle is set to 90 degrees. The offset angle can be set in a range from 90 to 160 degrees.

And it can be seen that, when the bending angle is 180 degrees, the resection surface 7 and the rear end of the insert plate 4 are completely separated from each other, in the so-called offset state as shown in FIG. 8. This means that contact between the residual bone 61 of the femur 6 and the insert plate, namely osseous impingement, can be prevented from occurring in the range of bending angles of the knee joint from 0 to 180 degrees, by carrying out a knee joint replacement operation by using the artificial knee joint of this embodiment. Thus the artificial knee joint of the present invention successfully achieved a movable range of bending angles from 0 to 180 degrees, which has been impossible with the conventional artificial knee joint.

However, the knee joint of a human being does not actually bend to an angle of 180 degrees, since surrounding tissues other than bone exist around the knee joint. The capability of the artificial knee joint of the present invention to prevent the occurrence of osseous impingement with bending angles of up to 180 degrees provides, in addition to the direct effect of allowing the knee to bend up to 180 degrees, an indirect effect of preventing the occurrence of soft tissue impingement, that is contact between the soft tissue surrounding the knee joint and the residual bone and/or the artificial knee joint that causes damage to the soft tissue.

It can be said that it suffices to prevent osseous impingement for the conventional artificial knee joint. However, in order to provide an artificial knee joint that achieves the function of a natural knee joint without discomfort or pain, it is important to prevent the soft tissue impingement as well. The artificial knee joint of the present invention can compress the occurrence of soft tissue impingement because of a sufficient allowance for the knee bending angle even in seiza posture where the knee bends to the largest angle (about 165 degrees).

In the artificial knee joint 1 of the present invention, it is preferable to control the amount of offset so that a distance a between the contact point between the cam-receiving slide surface 41 and the cam 21 and the rear end of the insert plate 4 and a distance b between the contact point between the cam-receiving slide surface 41 and the cam 21 and the resection surface 7 of the femoral component 2 satisfy a relationship of b>a in the second sliding state in which the femoral component 2 is offset. The distance between the residual bone and the insert plate can be separated by (b−a), by satisfying the relation b>a under such a condition that the resection surface 7 and the rear end of the insert plate 4 come nearest to each other, namely when the bending angle is 180 degrees, as shown in FIG. 8. This enables the reliable avoidance of osseous impingement from occurring in a range of bending angles from 0 to 180 degrees.

Figure 9:
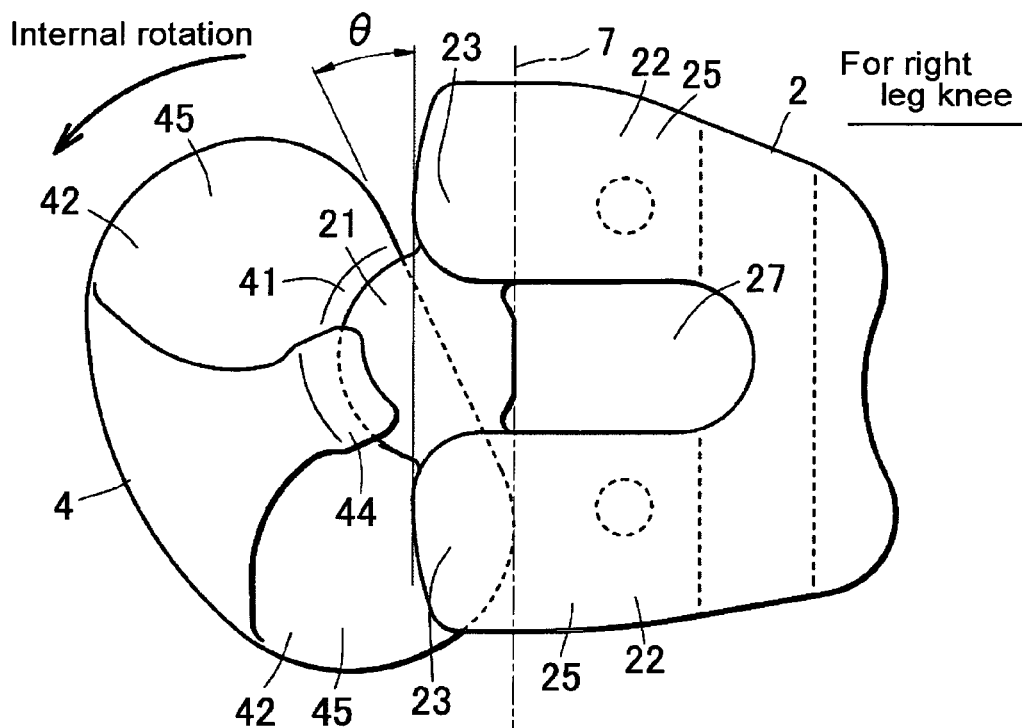
FIG. 9 shows the internal rotation of the artificial knee joint according to the first embodiment of the present invention, in top view (A) and side view (B).
Figure 9:
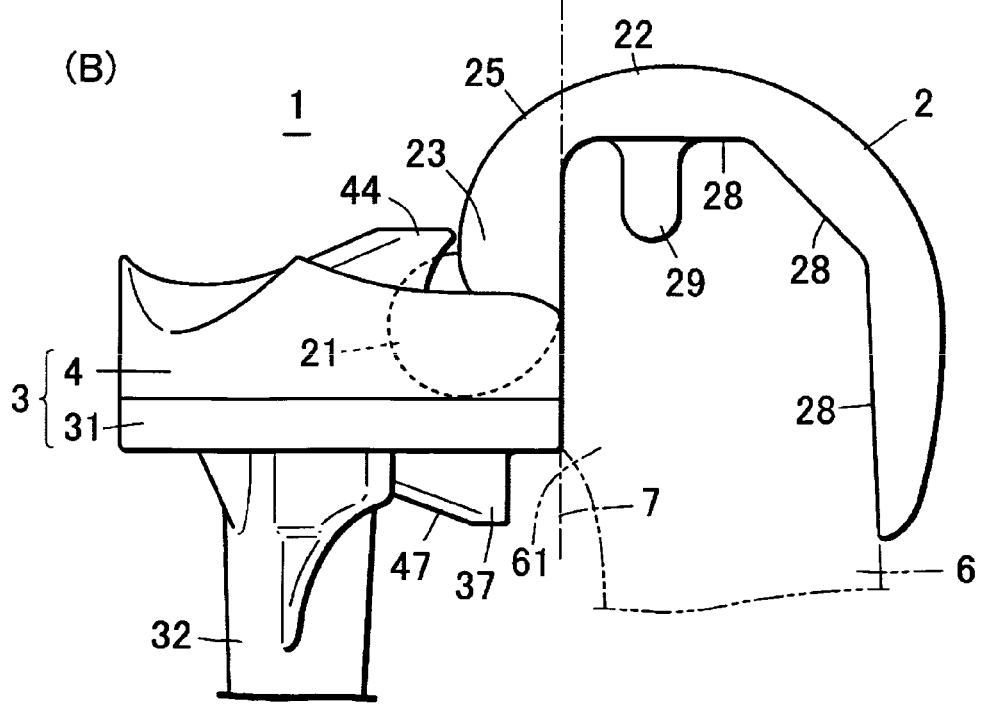

In the artificial knee joint 1 of the present invention, the cam 21 having a spheroidal shape is accommodated on the curved cam-receiving slide surface 41 under the post-offset condition as shown in FIG. 9, and therefore the femur can obtain internal rotation (the femur rotates within the horizontal plane). As a result, the artificial knee joint of the present invention achieves the bending motion of a natural knee joint without hampering the motion of the femur to turn a little internally when sitting in seiza posture. In this example, since the residual bone 61 and the insert plate contact each other with a rotation angle of θ=25 degrees, internal rotation and outward rotation over angles of θ=0 through 25 degrees can be achieved.

The artificial knee joint 1 of the present invention comprises the cam 21 and the cam-receiving slide surface 41 so as to take the second sliding state during deep bending of the knee, and has the femoral component 2 being offset so as to achieve the movable range of bending angles from 0 to 180 degrees, that has been impossible with the conventional artificial knee joint.

Second Embodiment

The artificial knee joint of this embodiment comprises the femoral component 2 and the tibial component 3 similarly to the first embodiment, although the cam 21 is fixed onto the rear end 23 of the femoral component 2 so as to be slidable, and the amount of offset can be adjusted by changing the amount of protrusion of the cam 21 beyond the femoral articular surface 25.

Figure 10:
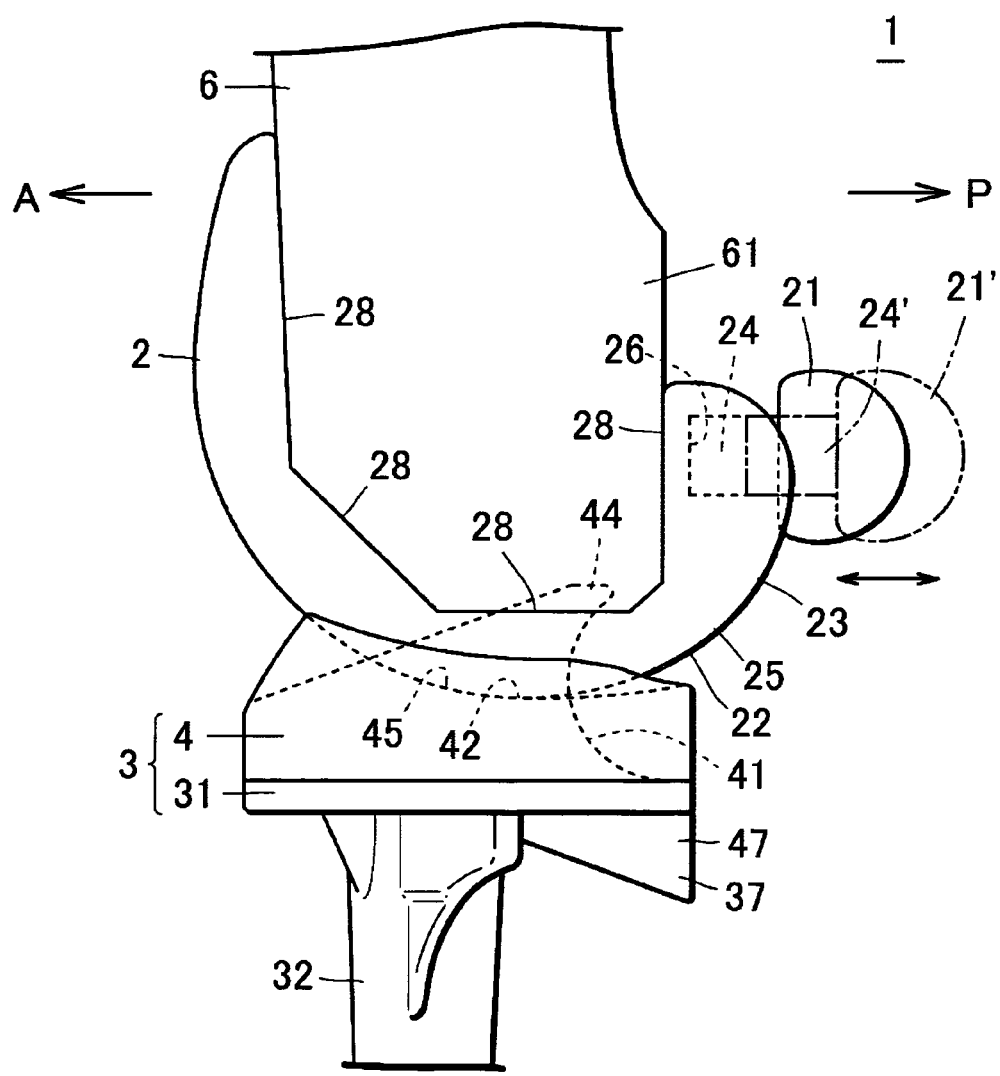
FIG. 10 is a side view of an artificial knee joint according to the second embodiment of the present invention.

A cam hole 26 is formed on the rear end 23 of the femoral component 2 as shown in FIG. 10, and the cam 21 is secured by inserting the cam stem 24 into the cam hole 26. The cam stem 24 and the cam hole 26 are secured together by forming an engaging mechanism on the surface of the cam stem 24 and on the medial surface of the cam hole 26, or by employing separate engagement members. Also the position of the cam stem 24 within the cam hole 26 can be changed by releasing the members from engagement, so as to move the cam stem 24, for example, to the position of cam stem 24'. Fixing the cam stem 24' in the cam hole 26 in this state enables it to function with the cam 21 protruding to the position of cam 21'.

Figure 11:
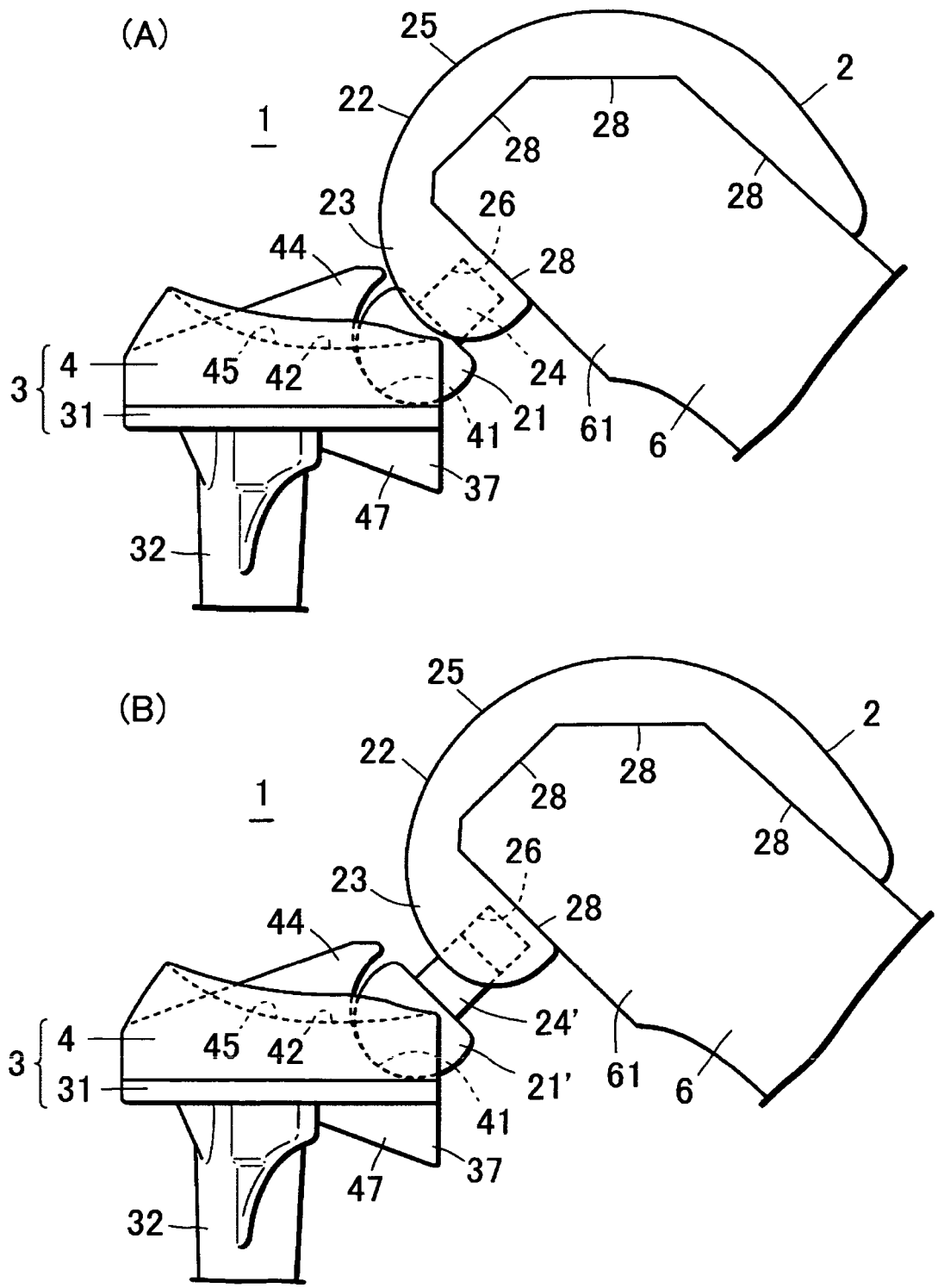
FIG. 11 shows two forms (A and B) of the artificial knee joint according to the second embodiment of the present invention.

The artificial knee joint 1 of this embodiment allows the selection between the second sliding state (A) in which the cam 21 does not protrude and the second sliding state (B) in which the cam 21' protrudes, in the second sliding state in which the cam 21 of the femoral component 2 and the cam-receiving slide surface 41 formed on the insert plate 4 of the tibial component 3 slide against each other, as shown in FIG. 11. In the artificial knee joint 1 shown in FIG. 11(B), the distance between the residual bone 61 of the femur 6 and the end of the insert plate 4 is larger than that in the case shown in FIG. 11(A), and this artificial knee joint is therefore suitable for a patient likely to suffer from osseous impingement. This constitution also makes it possible to reduce discomfort of the patient having the artificial knee joint 1 implanted, by selecting the position of either the cam 21 or the cam 21' so as to approximate the state of the knee joint prior to suffering the disease.

While this embodiment is an artificial knee joint that allows the change of the cam position in two steps of cam 21 and cam 21', another embodiment is conceivable where the position of the cam 21 can be changed in a plurality of steps or changed continuously.

Third Embodiment

The artificial knee joint of this embodiment comprises the femoral component 2 and the tibial component 3 similarly to the first embodiment, but is characterized in that the insert plate has a protrusion that inclines downward provided on the back surface at the mid position corresponding to the cam-receiving slide surface, and the tibial tray has a recess that accommodates the protrusion that tilts downward.

The artificial knee joint 1 of the present invention enables the knee to bend by means of the first sliding state and the second sliding state, while repetition of the sliding motion causes the insert plate 4 to wear. Therefore, it is necessary to set the thickness of the insert plate 4 so that the distance between the tibial articular surface 45 and the bottom of the cam-receiving slide surface 41 is not less than a predetermined thickness t that is set by taking the wear loss into account.

FIG. 12(B) shows the artificial knee joint 1 having the insert plate 4 formed by the conventional design technique. In the artificial knee joint 1 of the present invention, since the cam-receiving slide surface 41 is formed by deeply gouging, a thickness T' of the insert plate 4 is made significantly larger than the thickness t in order to secure the thickness t of the lower portion of the cam-receiving slide surface 41.

The artificial knee joint 1 of this embodiment, in contrast, has the protrusion 47 formed on the back surface of the cam-receiving slide surface 42 as shown in FIG. 12(A), thereby making it possible to secure the thickness t of the lower portion of the cam-receiving slide surface 42. In this embodiment, thickness T of the insert plate 4 excluding the protrusion 47 can be kept to a size comparable to the predetermined thickness t. This makes it possible to decrease the length of excision on the tibia by about (T'−T) when implanting the tibial component 3, thus contributing to the compression of fracture occurring after receiving the operation of implanting the artificial knee joint. While the tibia must be partially resected so as to match the profile of the protrusion 47, the volume of the bone part to be removed in the excision can be made less than that removed in a case where the insert plate 4 is thicker.

Figure 12:
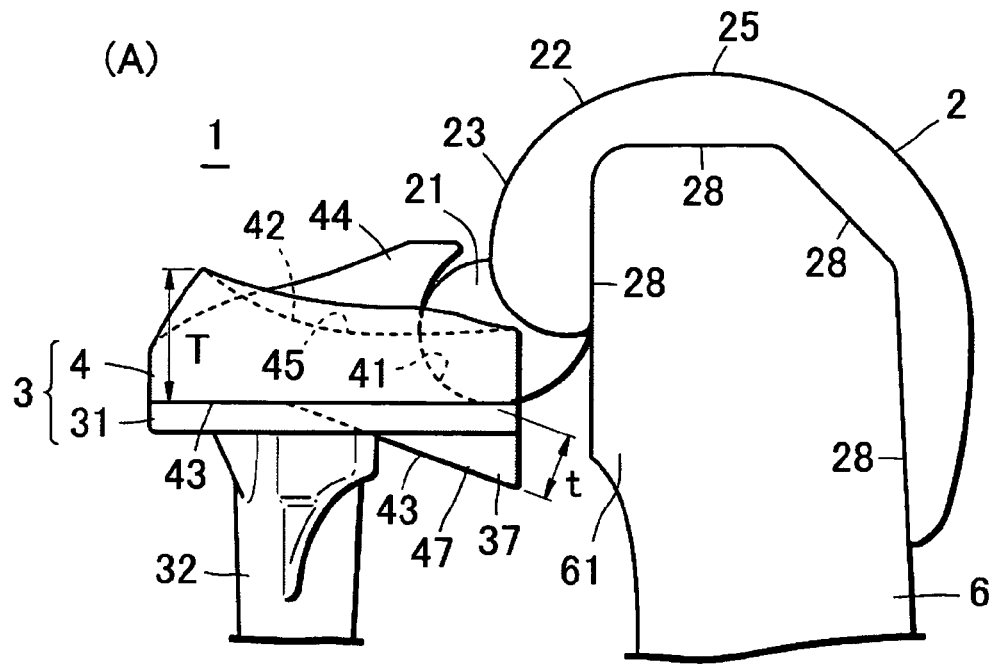
FIG. 12 shows a side view (A) of an artificial knee joint according to the third embodiment of the present invention and a side view (B) of a Comparative Example.
Figure 12:
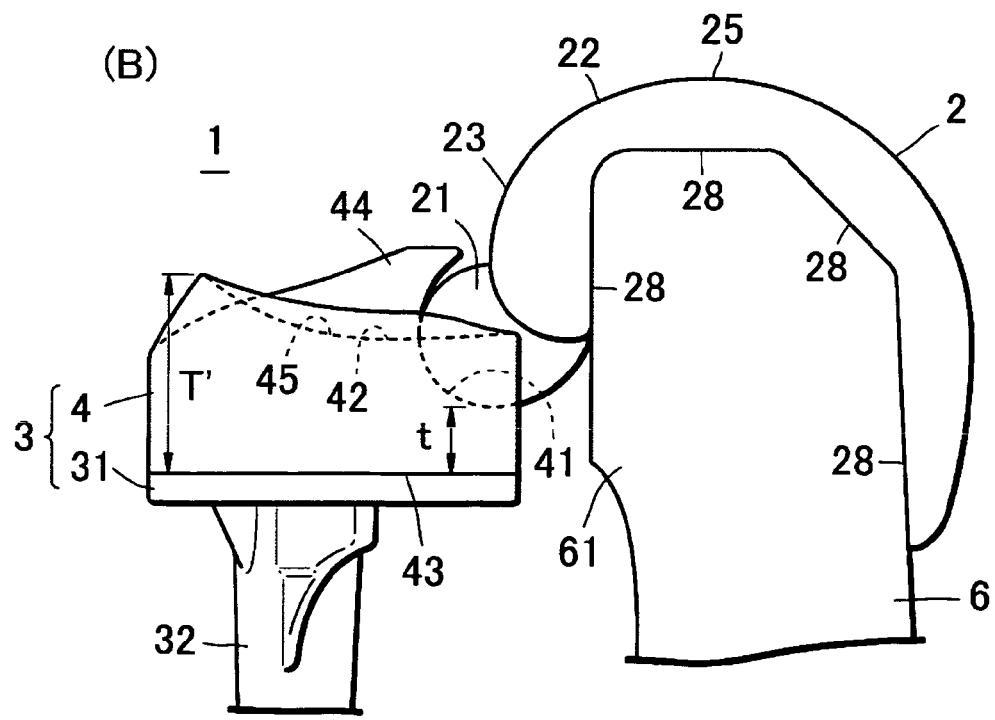

The protrusion 47 may be formed in various shapes as long as the required thickness of the lower part of the cam-receiving slide surface 42 can be secured. The protrusion may have, for example, a cubic, spherical or spheroidal shape. It is preferable that the protrusion 47 has a configuration that inclines downward as shown in FIG. 12. This is because such a configuration makes it easier to excise the tibia so as to match the profile of the protrusion 47, and the volume of the bone part to be removed can be reduced so as to minimize the amount of excision.

The tibial tray 31 has a recess 37 formed to match the profile of the protrusion 47 of the insert plate 4, so that the protrusion 47 is fitted into the recess 37 when fixing the insert plate 4 in the tibial tray 31. The recess 37 of the tibial tray 31 receives the load, which is exerted on the protrusion 47 of the insert plate 4, and distributes the load throughout the tibial tray 31 so as to prevent stress from concentrating at a portion of the tibia, thus providing the effect of reducing the possibility of fracture.

The tibial tray 31 has, on the back side thereof, a protrusion that matches the shape of the recess 37. This enables the thickness of the recessed portion 37 of the tibial tray 31 to be made substantially constant. The volume of bone removed from the tibia can be reduced while maintaining the function of stress distribution, by forming the tibial tray 31 with a minimum necessary thickness.

Fourth Embodiment

The artificial knee joint 1 of this embodiment comprises the femoral component 2 fixed on the distal portion of femur 6 and the tibial component 3 fixed on the proximal portion of the tibia, as shown in FIGS. 13 through 16.

The femoral component 2 comprises two femoral articular surfaces 25 of bulging and curved shapes (a medial femoral articular surface 25a and a lateral femoral articular surface 25b), a connection 21 (the cam in this example) that connects the rear ends of the two femoral articular surfaces, and a concave surface formed on the rear end of the lateral femoral articular surface 25b for the purpose of offset (referred to as lateral femoral offset surface 52). Formed on the distal end extending upward from the lateral femoral offset surface 52 is an offset tip 51 that is a flat beak-like member.

The tibial component 3 comprises the tibial tray 31 fixed onto the proximal portion of the tibia and the insert plate 4 fixed onto the top surface of the tibial tray 31.

The insert plate 4 comprises two tibial articular surfaces (a medial tibia articular surface 45a and a lateral tibia articular surface 45b) that make contact with the medial femoral articular surface 25a and the lateral femoral articular surface 25b, respectively, a spine 44 having a height that the connection 21 cannot ride over, a rear curved surface 41 (the cam-receiving slide surface in this example) formed on the back side P of the spine 44 so that the connection 21 slidably makes contact therewith, and a lateral tibia offset surface 82 formed on the rear end of the insert plate 4 so as to slide on the lateral femoral offset surface 52.

The artificial knee joint 1 of this embodiment takes the first sliding state when the knee is extended, in which the medial femoral articular surface 25a and the lateral femoral articular surface 25b make slidable contact with the medial tibial articular surface 45a and the lateral tibial articular surface 45b, respectively. When the knee joint bends to an angle from 90 to 160 degrees, contact of the lateral articular surfaces between the lateral femoral articular surface 25b and the lateral tibial articular surface 45b in the first sliding state shifts to the third sliding state where the lateral femoral offset surface and the lateral tibial offset surface can slide against each other. At roughly the same bending angle, the connection 21 of the femoral component 2 and the rear curved surface 41 of the spine 44 of the insert plate 4 make slidable contact with each other, thereby achieving the fourth sliding state. When the knee bends deep with a bending angle of 180 degrees, the third and fourth states of sliding coexist so that the resection surface 7 of the femoral component 3 and the rear end of the insert plate 4 are offset.

Figure 13:
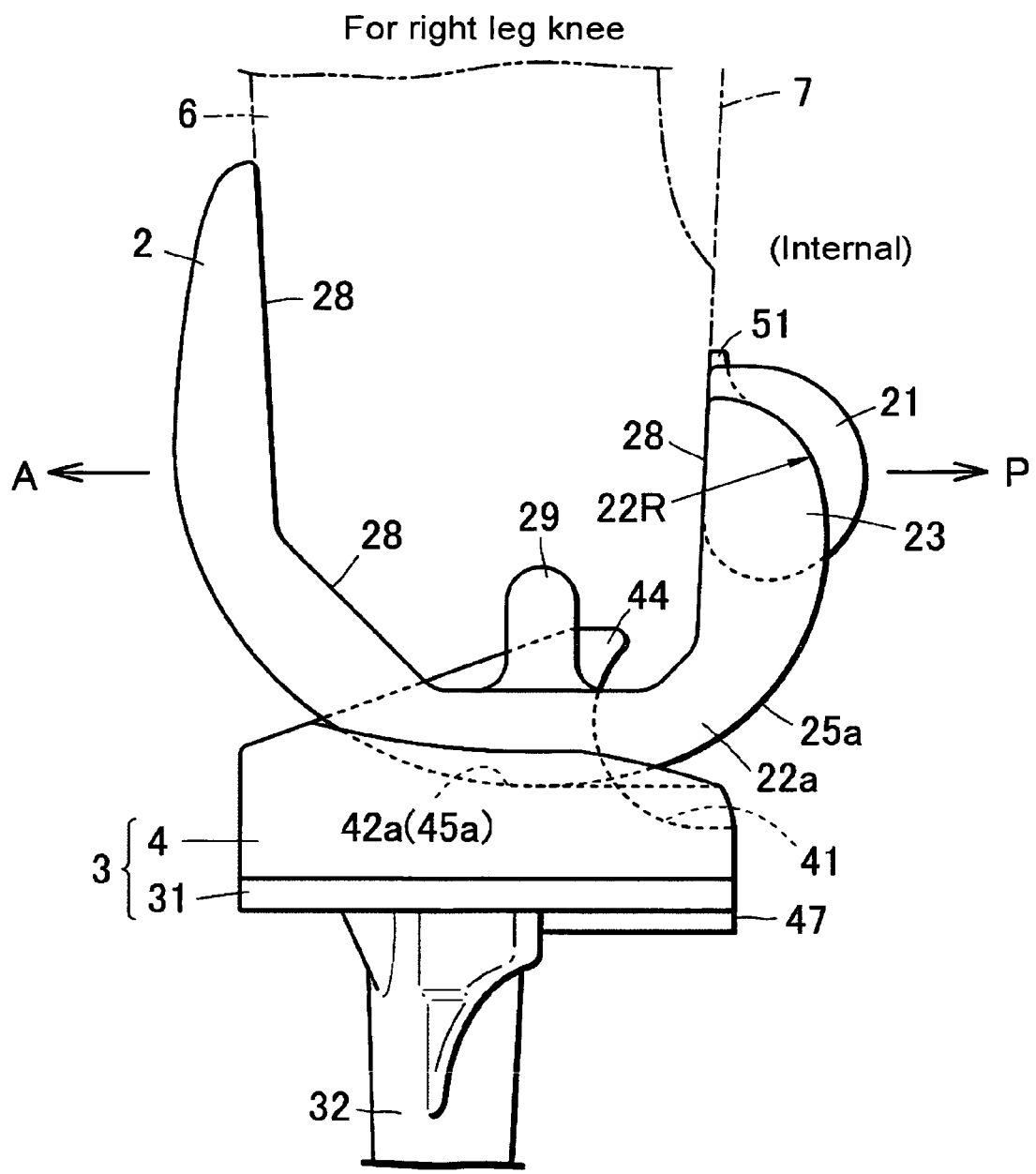
FIG. 13 is a side view of the medial side of an artificial knee joint according to the fourth embodiment of the present invention.
Figure 14:
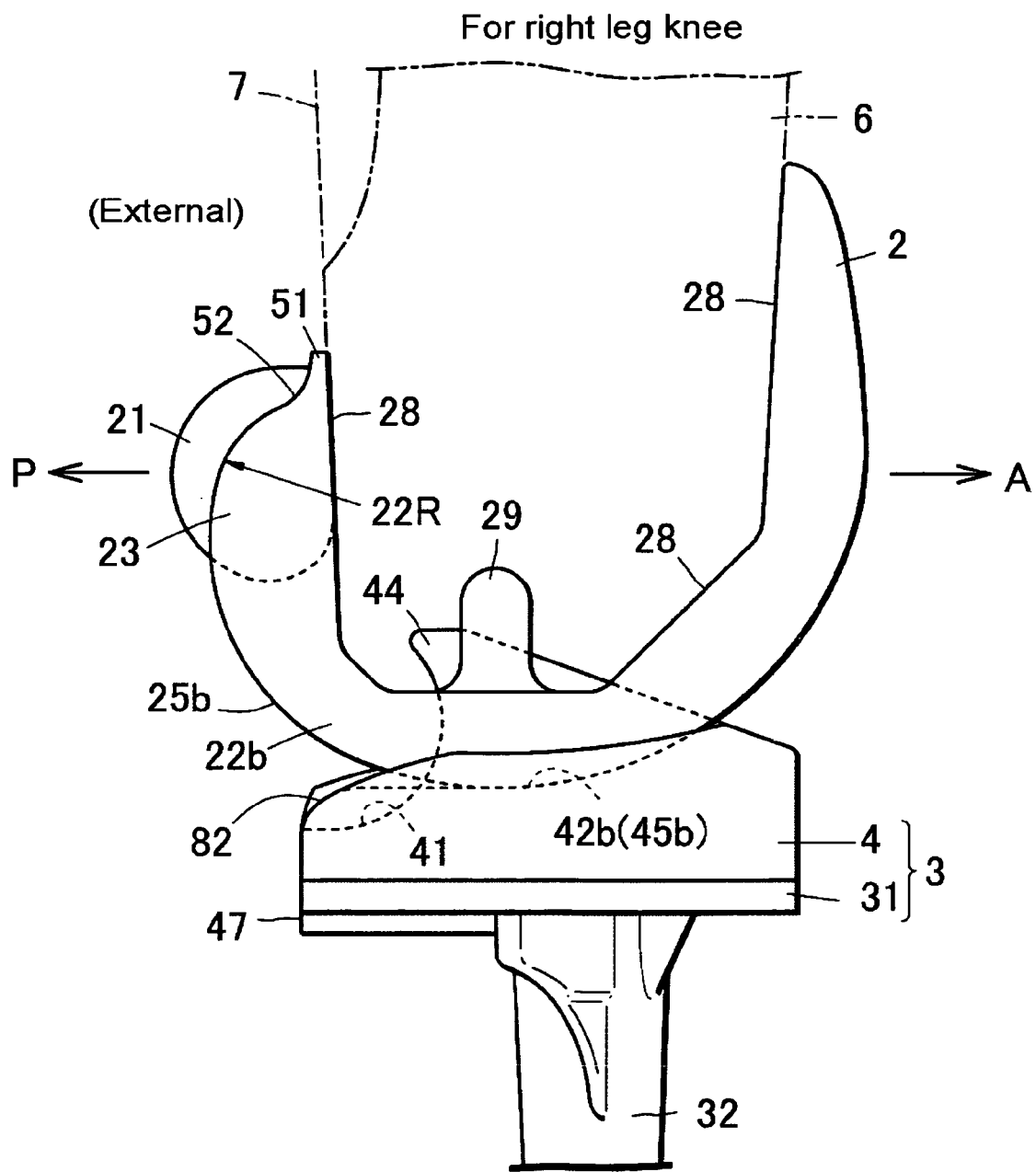
FIG. 14 is a side view of the lateral side of the artificial knee joint according to the fourth embodiment of the present invention.
Figure 15:
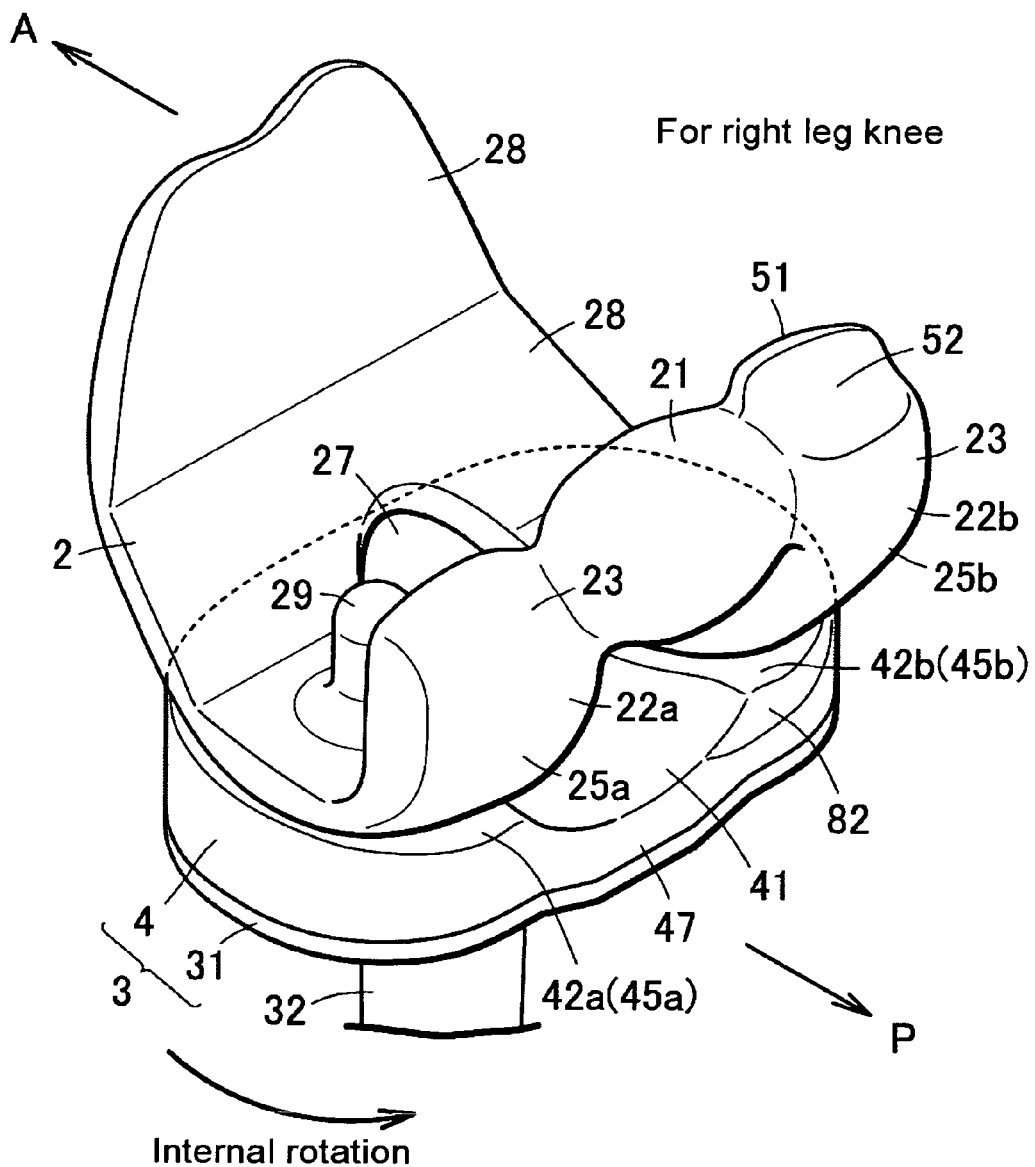
FIG. 15 is a perspective view of the artificial knee joint according to the fourth embodiment of the present invention.
Figure 16:
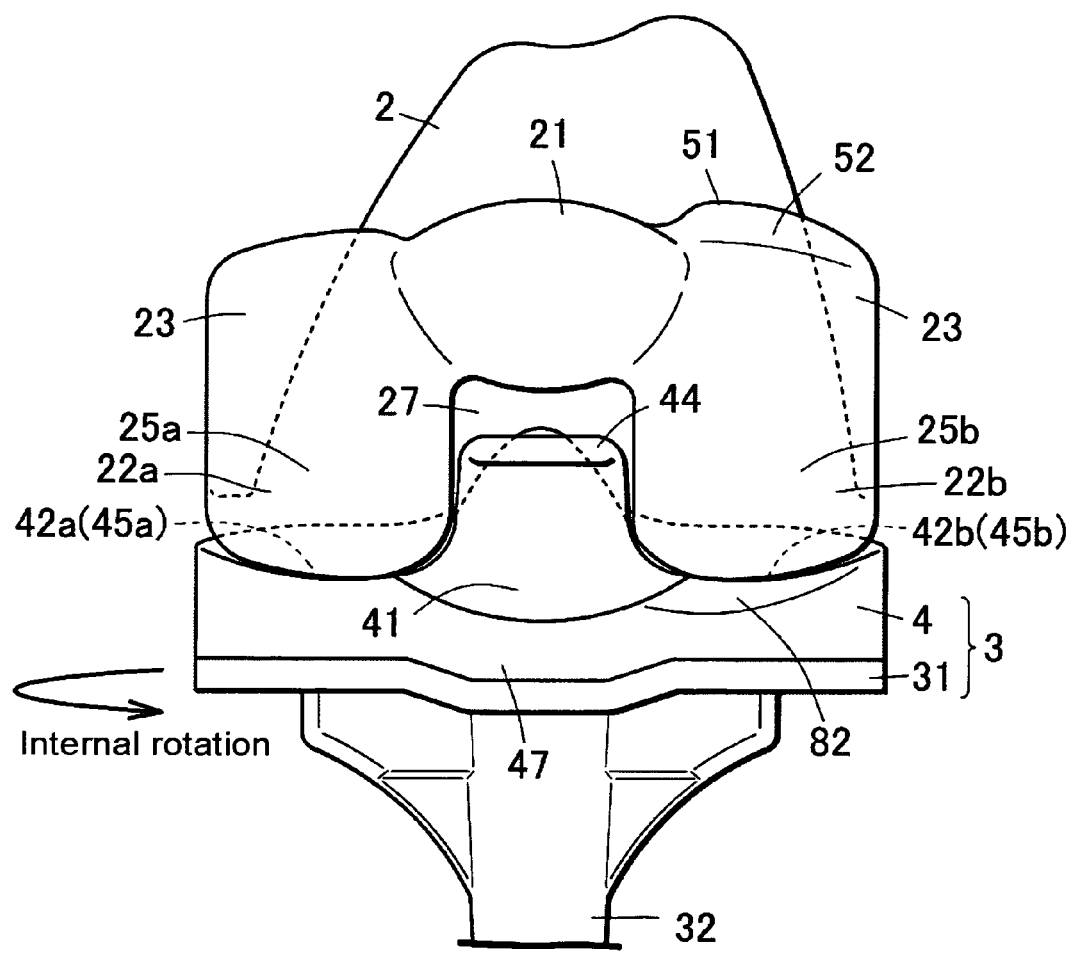
FIG. 16 is a front view of the artificial knee joint according to the fourth embodiment of the present invention.
Figure 17:
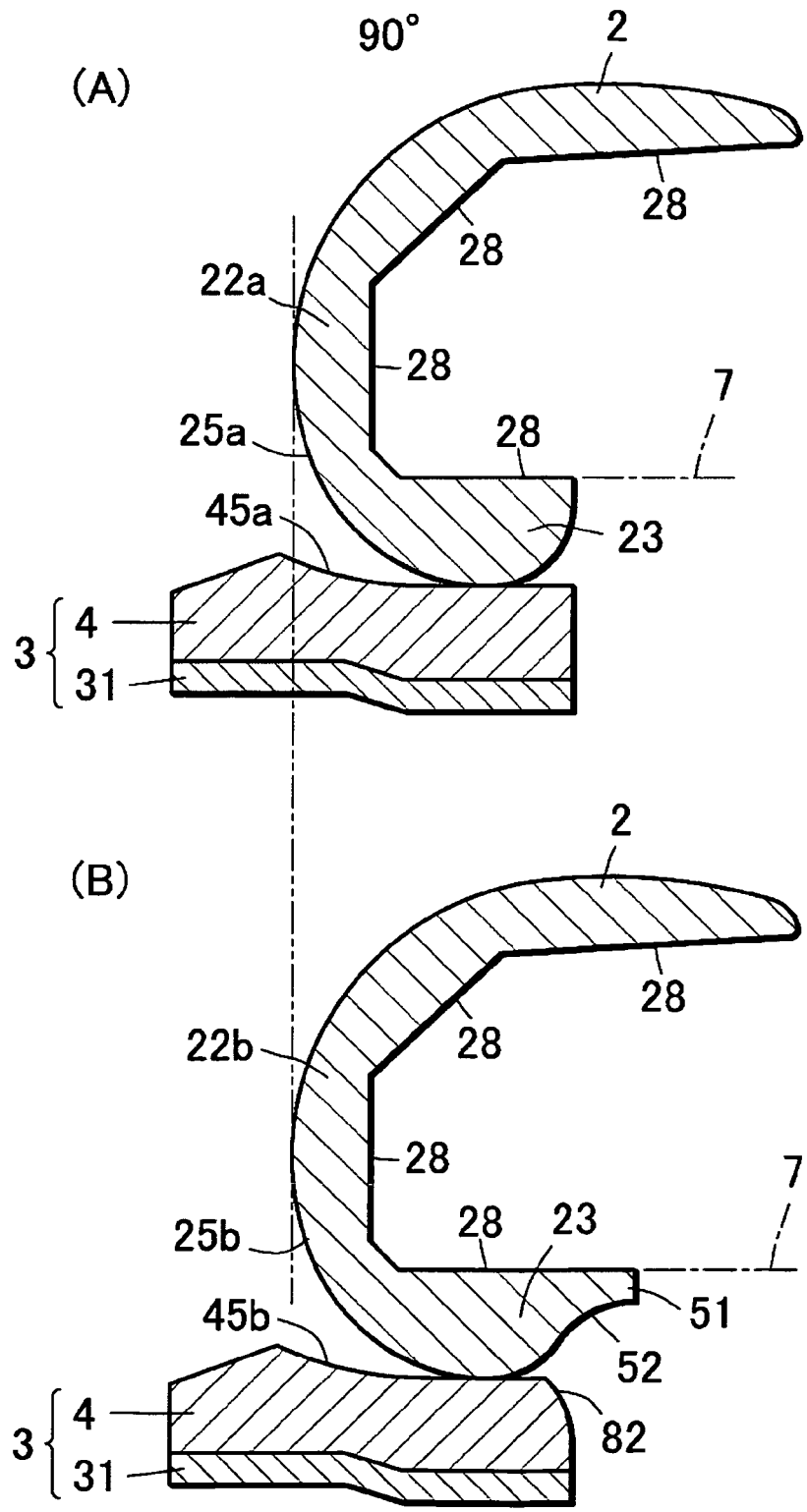
FIG. 17 shows the artificial knee joint according to the fourth embodiment of the present invention in bending motion at an angle of 90 degrees, in end views of the medial side (A) and the lateral side (B).
Figure 18:
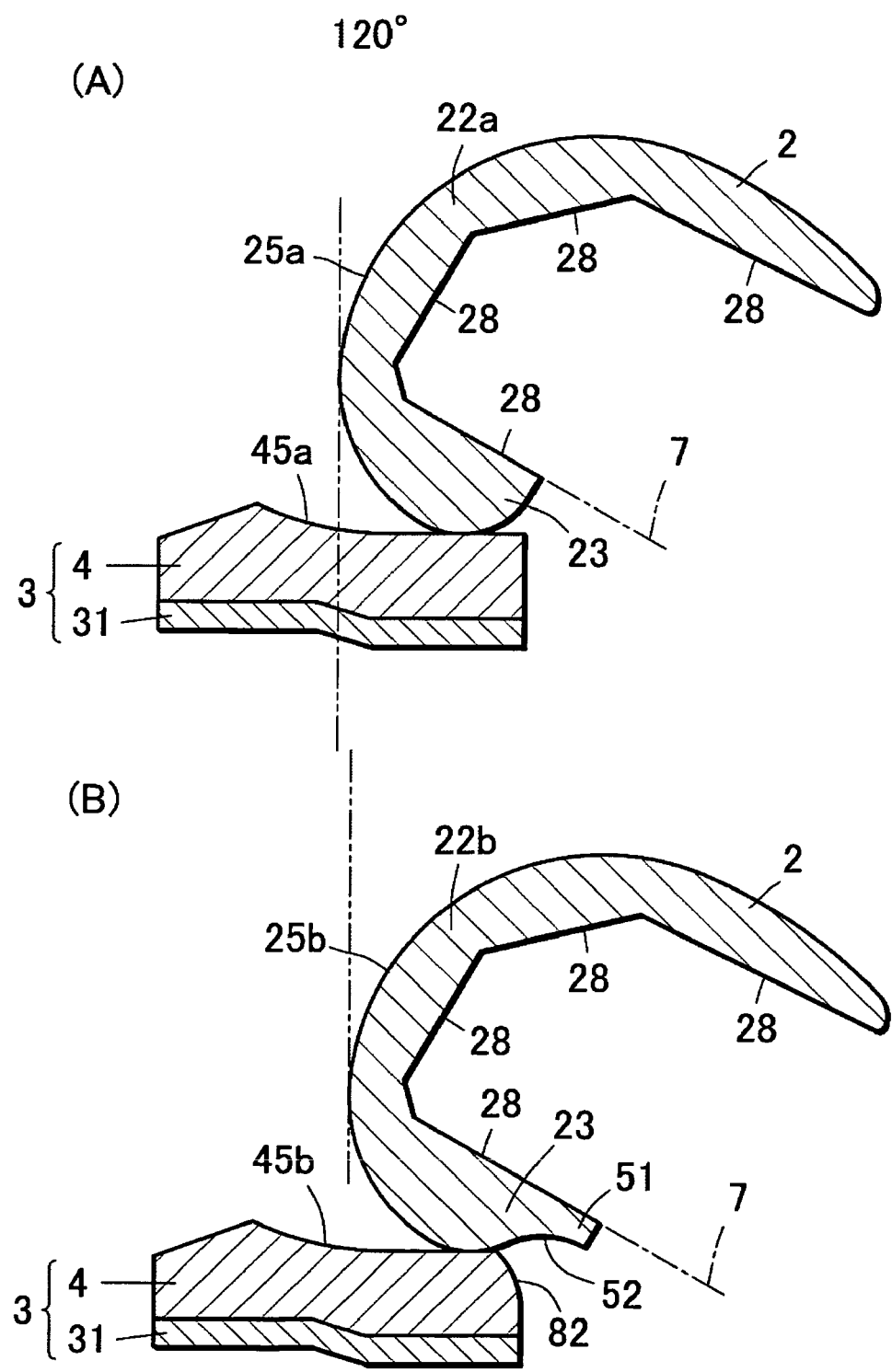
FIG. 18 shows the artificial knee joint according to the fourth embodiment of the present invention in bending motion at an angle of 120 degrees, in end views of the medial side (A) and the lateral side (B).
Figure 19:
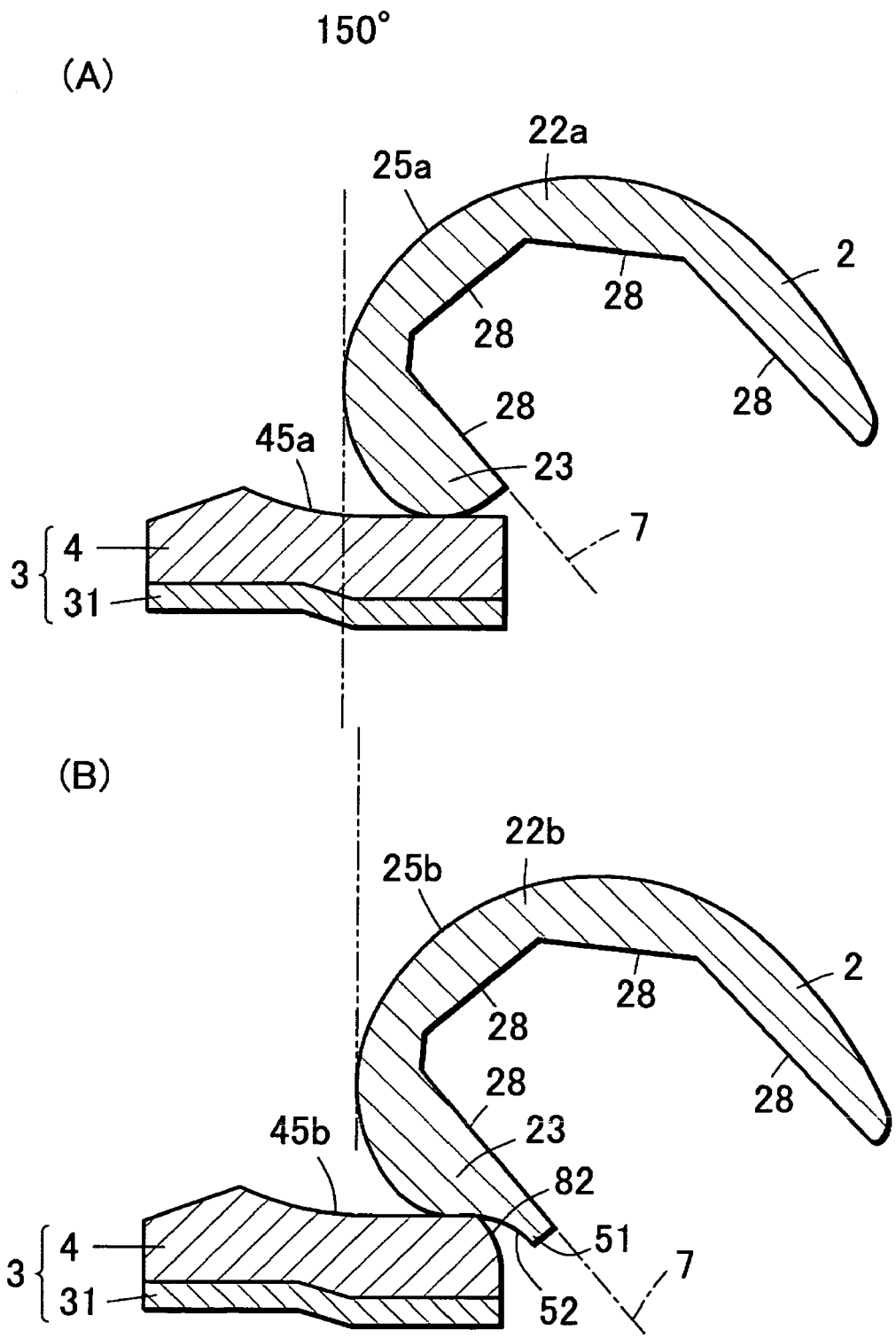
FIG. 19 shows the artificial knee joint according to the fourth embodiment of the present invention in bending motion at an angle of 150 degrees, in end views of the medial side (A) and the lateral side (B).

FIG. 13 and FIG. 14 are side views showing the artificial knee joint 1 of this embodiment designed for the right leg with a bending angle of 0 degrees, FIG. 13 being a side view from the medial side of the artificial knee joint 1 and FIG. 14 being a side view from the lateral side of the artificial knee joint 1. In these drawings, the femur 6 is shown to extend vertically upward. The femoral component 2 of the artificial knee joint 1 is used with the long portion thereof that extends upward being disposed at the front (in the direction of arrow A) and the rear end 23 disposed at the back (in the direction of arrow P).

The femoral component 2 has a deeply curved U-letter shape when viewed sideways, and is mounted so as to sandwich the end of the femur 6 on the front and back thereof, after excision of the distal portion of the femur 6. Formed on the lateral surface of the femoral component 2 are the medial condyle 22a and the lateral condyle 22b that extend forward and backward, and the surfaces thereof are referred to as the medial femoral articular surface 25a and the lateral femoral articular surface 25b. The medial and lateral femoral articular surfaces 25a, 25b are finished to be very smooth so as to allow smooth sliding motion when the knee joint is bent.

The femoral component has, on the rear end 23 thereof, the connection 21 having a spheroidal shape formed between the two condyles 22a and 22b. In this example, the connection 21 is formed as the cam 21 that protrudes in the backward direction P from the femoral articular surface 25. However, the connection 21 is not limited to this configuration and may have other shapes suitable for sliding motion, such as round cylinder, elliptical cylinder, sphere or the like.

The femoral component 2 has the femoral securing surface 28 formed on the medial side thereof for making contact with the femur 6. An ailing femur is subjected to an excision operation to remove the lesion from the bone surface, and the distal femur is trimmed so as to match the size and shape of the femoral securing surface 28 of the femoral component 2. A rear portion in the P side of the femur 6 is resected so as to match a plane called the resection surface 7 of femoral component 2, with a protruding portion called the residual bone 61 left to remain at the intersection of the profile of the femur 6 and the resection surface 7. Osseous impingement is often induced by the contact between the residual bone 61 and the tibial component 3, and may be mitigated by a technique that trims the femur 6 to reduce the protrusion of the residual bone 61. However, such a trimming operation requires an advanced osteotomy technique and may leave the residual bone 61 having such a shape as shown in the drawing in many cases.

A ball 29 may be provided as required on the femoral securing surface 28 of the femoral component 2. The ball 29 is inserted into the femur so as to stabilize the state of the femoral component mounted therein. The femoral component 2 is fixed onto the femur as required by means of a bone cement. The femoral component 2 is formed from metal having high biocompatibility such as titanium alloy or cobalt-chromium alloy, or ceramics such as alumina or zirconia.

The insert plate 4 of the tibial component 3 is a member used to allow the femoral component 2 to slide thereon. The insert plate 4 has two sockets, a medial socket 42a and a lateral socket 42b, extending in the front-back direction, to allow the two condyles, the medial condyle 22a and the lateral condyle 22b, of the femoral component 2 to slide therein. The medial condyle 22a and the lateral condyle 22b have the medial tibial articular surface 45a and the lateral tibial articular surface 45b, respectively, which are very smooth, formed on the surface thereof, so that the medial femoral articular surface 25a and the lateral femoral articular surface 25b of the femoral component 2 can slide smoothly thereon.

The insert plate 4 has the spine 44 formed near the center thereof, that protrudes from the slot 27 that is formed at the center of the femoral component 2 and extends in the front-back direction. Formed on the surface of the spine 44 on the back side P is the rear curved surface 41 so that the connection 21 slides thereon.

The rear curved surface 41 of the spine 44 is formed in a shape that accommodates the connection 21 of the femoral component 2. The rear curved surface 41 and the connection 21 are designed so as to make contact with each other when the artificial knee joint 1 bends beyond a predetermined angle, for example 90 degrees. Surfaces of the rear curved surface 41 and the connection 21 are both finished smoothly so as to allow smooth sliding motion. The insert plate 44 is formed from polyethylene of ultra-high molecular weight (UHMWPE).

The tibial tray 31 of the tibial component 3 is fixed, on the bottom surface thereof, onto the proximal portion of the tibia, and receives the insert plate 4 on the top surface. The tibial tray 31 has the function of distributing the load exerted by the femoral component 2 on the insert plate 4 so as to prevent stress from concentrating at a portion of the tibia. To fix the tibial tray 31, the lesion of the joint in the proximal portion of the tibia is resected first, followed by the insertion of the stem 32 of the tibial tray 31 into the tibia. After positioning the tibial tray so that the top surface thereof becomes substantially horizontal, the tibial tray 31 is fixed onto the tibia by means of a screw or bone cement.

The tibial tray 31 is formed from metal having high biocompatibility such as titanium alloy or cobalt-chromium alloy, or ceramics such as alumina or zirconia.

In the artificial knee joint 1 of the present invention, the sliding state that constitutes the main contact shifts from the first sliding state to the third sliding state through transition angles in a range from 90 to 160 degrees. The transition angle at which the sliding state shifts is the offset angle. The first sliding state takes place over a large contact area and is therefore suited to a situation in which a large load is applied to the knee such as standing upright or walking. The third sliding state, in contrast, is not capable of bearing a heavy load on the knee but allows deep knee bending as compared to the first sliding state. Therefore, the offset angle is determined by balancing the load on the knee and the extent to which osseous impingement is to be avoided.

An offset angle less than 90 degrees causes a shift to the third sliding state when the knee is still under a large load which compromises the stability of the knee, and is therefore not desirable. An offset angle larger than 160 degrees allows the occurrence of osseous impingement in the first sliding state, and is therefore not desirable.

The artificial knee joint 1 of the present invention allows the knee to bend at angles in a range from 0 to 180 degrees as shown in FIGS. 13, 14 and 17 through 20. FIGS. 17 through 20 show end views on the medial side (A) and end views on the lateral side (B). The offset angle of the artificial knee joint 1 is 90 degrees.

When the bending angle is 0 degrees (the knee is extended) as shown in FIG. 13 (side view of the medial side) and FIG. 14 (side view of the lateral side), the medial femoral articular surface 25a and the lateral femoral articular surface 25b make contact with the medial tibial articular surface 45a and the lateral tibial articular surface 45b, respectively, thus achieving the first sliding state. This state takes place when the person is standing upright or walking, causing a heavy load on the knee joint. The artificial knee joint of the present invention takes the first sliding state when the bending angle is 0 degrees, and is therefore capable of bearing the heavy load applied to the knee joint.

When the bending angle reaches the offset angle of 90 degrees, the sliding state on the lateral side shown in FIG. 17(B) begins to shift from the first sliding state to the third sliding state in which the lateral femoral offset surface 52 and the lateral tibial offset surface 82 make contact with each other. Meanwhile no change occurs in the sliding state on the medial side shown in FIG. 17(A).

At the same time, the connection 21 and the rear curved surface 41 make contact with each other, so as to achieve the fourth sliding state.

As the bending angle of the knee joint is increased beyond the offset angle of 90 degrees of the artificial knee joint, sliding on the lateral side is caused to proceed first by the lateral femoral offset surface 52 fitting to the lateral tibial offset surface 82, then by the offset tip 51 hitching onto the rear of the lateral tibial offset surface 82 as shown in FIG. 18(B) and FIG. 19(B). At this time, the lateral femoral articular surface 25b is displaced toward the back side P by the thickness of the offset tip 51. This outward displacement, together with the fourth sliding state (sliding state of the connection 21 not shown in the drawing and the rear curved surface 41 of the spine 44), causes the medial femoral articular surface 25a to be displaced forward as shown in FIG. 18(A) and FIG. 19(A). As the medial side and lateral side of the femoral component 2 are displaced in different directions, the femoral component 2 undergoes rotation. When the medial side is displaced forward in direction A and the lateral side is displaced backward in direction P, in particular, the femoral component 2 is caused to undergo internal rotation. In this way, the artificial knee joint 1 of this embodiment enables internal rotation to take place during bending as in a healthy knee joint.

Figure 20:
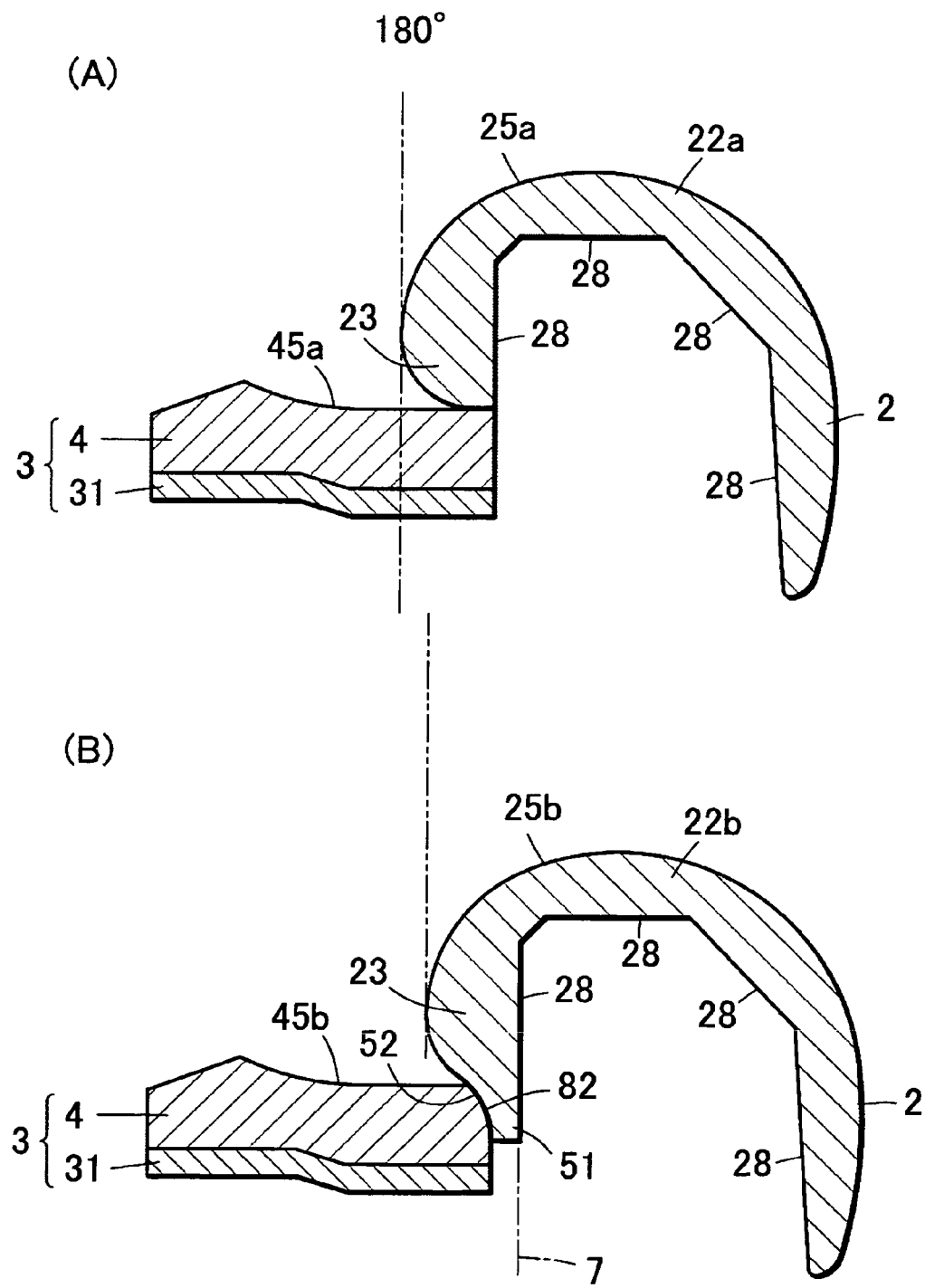
FIG. 20 shows the artificial knee joint according to the fourth embodiment of the present invention in bending motion at an angle of 180 degrees (deep knee bending), in end views of the medial side (A) and the lateral side (B).

When the knee joint is bent at 180 degrees as shown in FIG. 20, the lateral side (FIG. 20(B)) is offset by the thickness of the offset tip 51, so that the resection surface 7 and the rear end of the insert plate 4 depart from each other. The medial side (FIG. 20(A)), on the other hand, is displaced forward in direction A and is therefore offset less than the lateral side. In case there is the possibility of osseous impingement occurring on the medial side with a bending angle below 180 degrees, the rear end 23 of the femoral component 2 may be made thicker so as to increase the distance between the resection surface 7 and the rear end of the insert plate 4.

Replacing the knee joint with the artificial knee joint of this embodiment prevents the residual bone 61 of the femur 6 and the insert plate from touching, that is to prevent osseous impingement from occurring, in a range of bending angles of the knee joint from 0 to 180 degrees. Thus the artificial knee joint of the present invention successfully achieves a movable range of bending angles from 0 to 180 degrees, that has been impossible with the conventional artificial knee joint.

However, the knee joint of a human being does not actually bend to an angle of 180 degrees, since surrounding tissues other than bone exist around the knee joint. The capability of the artificial knee joint of the present invention to prevent osseous impingement up to the bending angle of 180 degrees provides, in addition to the direct effect of allowing the knee to bend up to 180 degrees, an indirect effect of avoiding soft tissue impingement, that is contact between the soft tissue surrounding the knee joint and the residual bone and/or the artificial knee joint causing damage to the soft tissue.

It can be said that it suffices to prevent the occurrence of osseous impingement for the conventional artificial knee joint. However, in order to provide an artificial knee joint that achieves the function of a natural knee joint without causing discomfort or pain to the patient, it is important to prevent the occurrence of soft tissue impingement as well. The artificial knee joint of the present invention can compress the occurrence of soft tissue impingement because of a sufficient allowance of the bending angle even in seiza posture that causes the knee to bend to the largest angle (about 165 degrees)

As can be seen from the third sliding state shown in FIGS. 18 through 20(A), the offset tip 51 hitches onto the rear portion of the insert plate 4. This compresses localized severe wear of the spine 44. In general, as the knee joint bends deeper, the femoral component 2 is forced to move forward in direction A. In the conventional artificial knee joint, the force is received solely by the connection 41 and the rear curved surface 41 of the spine 44, thus resulting in severe wear of the rear curved surface 41. In the artificial knee joint of this embodiment, in contrast, the offset tip 51 also receives the force exerted in the forward direction A on the femoral component, and therefore the stress acting on the rear curved surface 41 is distributed thereby compressing severe wear from taking place.

As a modification of this embodiment, there is an artificial knee joint of such a constitution as the femoral component comprises the medial femoral offset surface (not shown) having a recessed shape formed on the rear end of the medial femoral articular surface, and the lateral tibial offset surface against which the medial femoral offset surface slides is provided at the rear end of the insert plate 4, and the contact of the medial articular surface in the first sliding state shifts through bending angles in a range from 90 to 160 degrees to the third sliding state in which the medial femoral offset surface and the medial tibial offset surface make slidable contact with each other.

In other words, the artificial knee joint may have such a constitution as the offset tip 51 being formed not only on the lateral side of the femoral component 2 but also on the medial side of the femoral component, so that both the medial side and the lateral side are offset. In this modification, since the offset tip 51 hitches onto the rear end of the insert plate 4 at two points, the force that moves the femoral component forward in direction A is more effectively distributed and is thus desirable. While the medial and lateral offset tips may be formed in the same size and shape, it is preferable to make possible natural internal rotation by forming the offset tips in different sizes and shapes.

The depth of the rear curved surface 41 of the spine 44 that receives the connection 21 can be reduced by forming the connection 21 of the femoral component 2 in a spherical shape or a substantially cylindrical shape that does not protrude beyond the femoral articular surface 25. Such a configuration prevents the thickness of the insert plate 4 from increasing, so that the volume of bone to be removed from the tibia can be decreased.

On the contrary, the rear curved surface 41 of the spine 44 of the insert plate 4 may also be formed as the cam-receiving slide surface 41 whereon the cam 21 slides by forming the connection 21 of the femoral component 2 as the cam 21 having a spherical shape or a substantially cylindrical shape that protrudes beyond the femoral articular surface 25. Forming the connection 21 as the cam leads to an increasing contact area in the fourth sliding state, and therefore severe wear of the rear portion of the spine 44 can be compressed thereby providing an artificial knee joint that can be used over a long period of time.

The artificial knee joint of the present invention makes it possible to bend the knee deeply to an extent impossible with the conventional artificial knee joint, so that the knee can be bent to an angle of up to 180 degrees in theory, thereby preventing the occurrence of not only the osseous impingement but also of the soft tissue impingement. Moreover, the artificial knee joint of the present invention enables internal rotation of the femur to take place similarly to that occurring naturally in a healthy knee joint. As a result, such an artificial knee joint is provided that causes less discomfort to the patient whose knee joint has been replaced with the artificial knee joint.

The artificial knee joint of the present invention is less likely to undergo severe wear of component parts, and therefore can be used over a long period of time, thus providing a boon for patients who are forced to receive repetitive implant operations. This artificial knee joint also has various contrivances to reduce the amount of excision, and therefore provides benefits to patients whose femur has been reduced in volume.

What is claimed is:

1. An artificial knee joint comprising:
a femoral component configured to be fixed onto a distal portion of a femur;
a tibial tray configured to be fixed onto a proximal portion of a tibia; and
an insert plate fixed onto a top surface of the tibial tray to receive the femoral component sliding thereon,
the femoral component including first and second curved femoral articular surfaces and a cam having a spheroidal or substantially cylindrical shape disposed on the rear end of the femoral articular surface and protruding from the femoral articular surface,
the insert plate including first and second tibial articular surfaces that contact the first and second femoral articular surfaces, respectively, and a cam-receiving slide surface that contacts the cam,
wherein the artificial knee joint has a first sliding state in which the femoral articular surface slides on the tibial articular surface when the knee is extended,
a main contacting surface shifts from the first sliding state to a second sliding state in which the cam slides on the cam-receiving slide surface when the knee is bent at an angle between 90 to 160 degrees, and
a resection surface of the femoral component and a rear end of the insert plate are offset in the second sliding state when the knee is bent deeply with a bending angle of 180 degrees.

2. The artificial knee joint according to claim 1, wherein, in the second sliding state with a bending angle of 180 degrees, an amount of offset is controlled so that a first distance between a contact point at which the cam contacts the cam-receiving slide surface and the rear end of the insert plate is less than a second distance between the contact point at which the cam contacts the cam-receiving slide surface and the resection surface of femoral component, such that the resection surface and offset of the rear end of the insert plate are a distance that is the difference between the second distance minus the first distance or greater.

3. The artificial knee joint according to claim 1, wherein the cam is configured to be replaceably fixed on the rear end of the femoral component, and the amount of a protrusion of the cam beyond the femoral articular surface is changed so as to control the amount of offset.

4. The artificial knee joint according to claim 1, wherein the insert plate has a protrusion disposed on a lower surface of the insert plate at a mid position corresponding to the cam-receiving slide surface, the lower surface being opposite at least one of the first and second tibial articular surfaces, and the tibial tray has a recess that receives the protrusion.

5. An artificial knee joint comprising:
a tibial component and a femoral component;
the femoral component having a cam disposed on a posterior surface of the femoral component;
the tibial component having a tibial tray configured to be fixed onto a proximal portion of the tibia, the tibial tray comprising an top surface and a lower surface; and
an insert plate fixed onto a top surface of the tibial tray, the insert plate including an upper articulating surface configured to receive the femoral component so as to enable the femoral component to slides thereon and a lower surface opposite the upper articulating surface,
the insert plate includes a cam-receiving slide surface capable of sliding the cam disposed on the posterior surface of the femoral component, the lower surface of the insert plate has a flat surface and a protrusion, the protrusion extends beyond the flat surface and is disposed on the lower surface at a mid position below the cam-receiving slide surface; and
the tibial tray has a recess on the upper surface that receives the insert plate protrusion, and a protrusion extending from the lower surface.

* * * * *